(12) United States Patent
Iwasaki et al.

(10) Patent No.: US 11,759,118 B2
(45) Date of Patent: Sep. 19, 2023

(54) MAGNETIC SENSOR AND INSPECTION DEVICE

(71) Applicant: KABUSHIKI KAISHA TOSHIBA, Tokyo (JP)

(72) Inventors: Hitoshi Iwasaki, Nerima Tokyo (JP); Satoshi Shirotori, Yokohama Kanagawa (JP); Akira Kikitsu, Yokohama Kanagawa (JP); Yoshihiro Higashi, Komatsu Ishikawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 219 days.

(21) Appl. No.: 17/444,987

(22) Filed: Aug. 12, 2021

(65) Prior Publication Data
US 2022/0233087 A1 Jul. 28, 2022

(30) Foreign Application Priority Data
Jan. 26, 2021 (JP) .................. 2021-010239

(51) Int. Cl.
| | |
|---|---|
| G01R 33/00 | (2006.01) |
| A61B 5/05 | (2021.01) |
| G01N 27/72 | (2006.01) |
| A61B 5/245 | (2021.01) |
| G01R 33/09 | (2006.01) |

(52) U.S. Cl.
CPC ............ *A61B 5/05* (2013.01); *A61B 5/245* (2021.01); *G01N 27/72* (2013.01); *G01R 33/0094* (2013.01); *G01R 33/093* (2013.01); *A61B 2562/0223* (2013.01)

(58) Field of Classification Search
CPC combination set(s) only.
See application file for complete search history.

(56) References Cited

U.S. PATENT DOCUMENTS

| 10,809,321 B2 * | 10/2020 | Kikitsu ............... G01R 33/093 |
| 2018/0081001 A1 * | 3/2018 | Iwasaki .................. A61B 5/243 |
| 2018/0252780 A1 * | 9/2018 | Iwasaki ............... G01R 33/093 |
| 2018/0271395 A1 | 9/2018 | Iwasaki et al. |
| 2019/0369172 A1 * | 12/2019 | Kikitsu ............. G01R 33/0023 |

FOREIGN PATENT DOCUMENTS

JP 2018-155719 10/2018

\* cited by examiner

*Primary Examiner* — Alvaro E Fortich
(74) *Attorney, Agent, or Firm* — Finnegan, Henderson, Farabow, Garrett & Dunner, LLP

(57) ABSTRACT

According to one embodiment, a magnetic sensor includes a first sensor part, and a conductive member. The first sensor part includes a first magnetic element, a first side magnetic part, and a first counter side magnetic part. The conductive member includes a first corresponding portion along the first magnetic element. The first magnetic element includes a first magnetic layer, a first counter magnetic layer, a direction from the first magnetic layer toward the first counter magnetic layer being along a first direction, and a first intermediate magnetic layer located between the first magnetic layer and the first counter magnetic layer. The first side magnetic part includes a first side magnetic layer. The first counter side magnetic part includes a first counter side magnetic layer. The first intermediate magnetic layer is between the first side magnetic layer and the first counter side magnetic layer in a second direction.

20 Claims, 18 Drawing Sheets

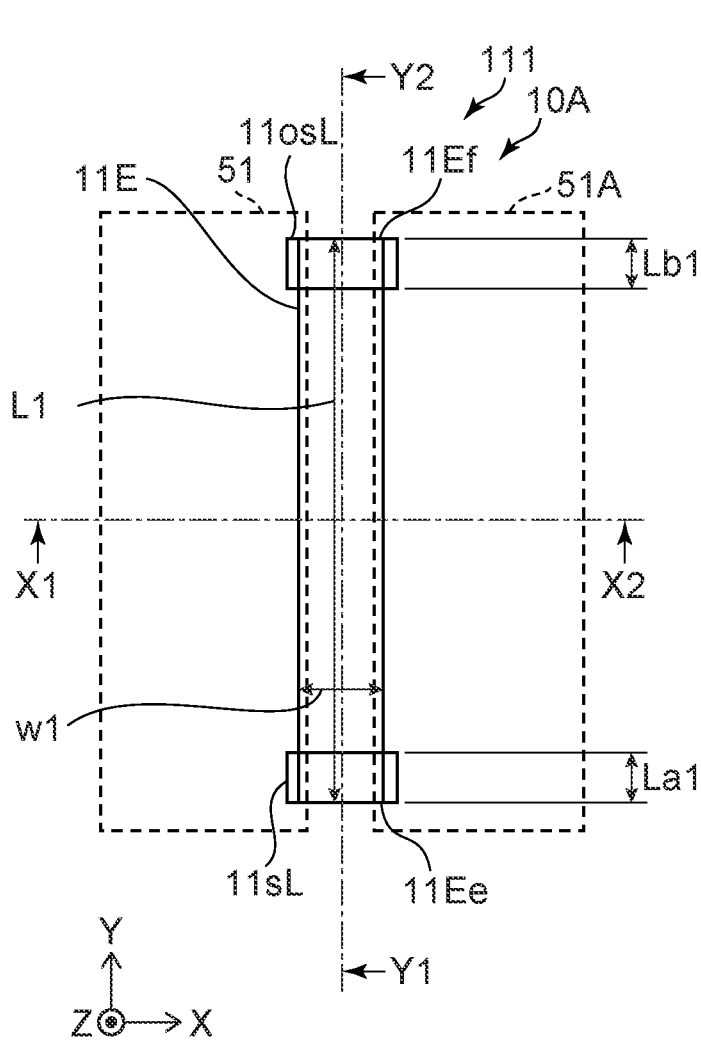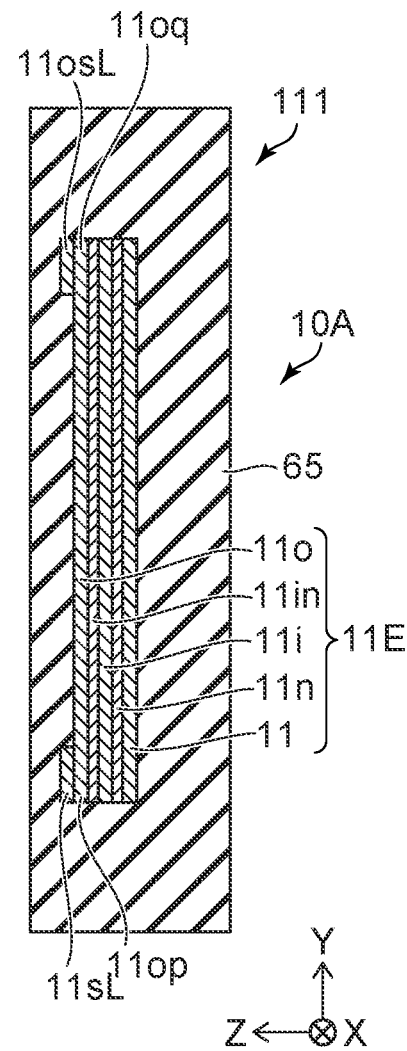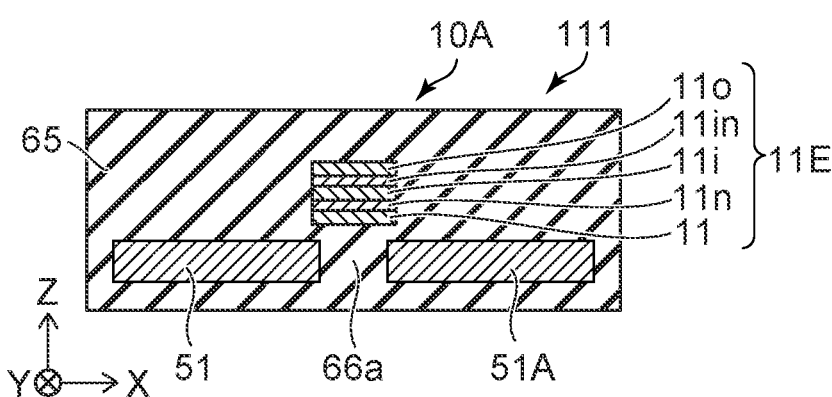

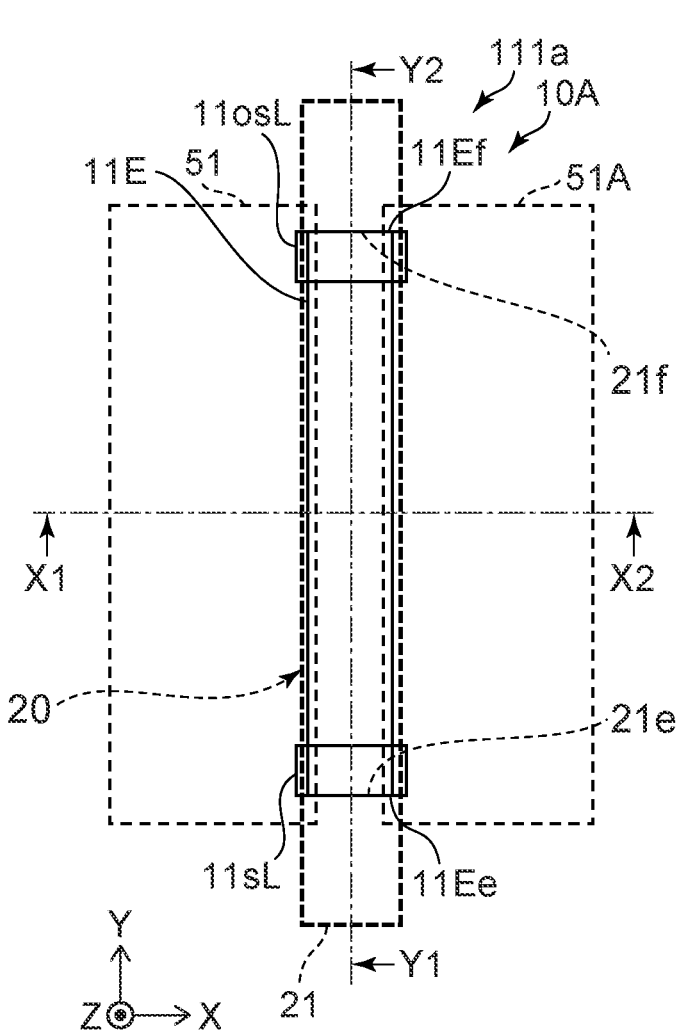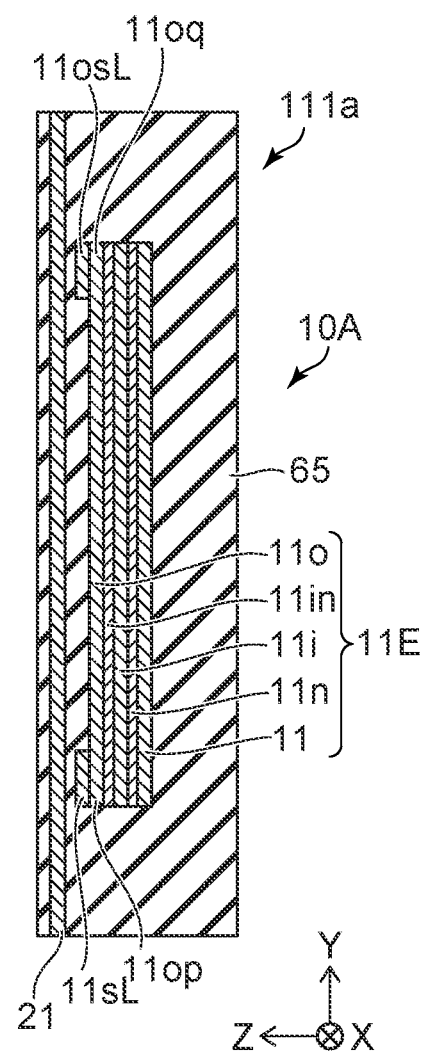
FIG. 6A  FIG. 6B
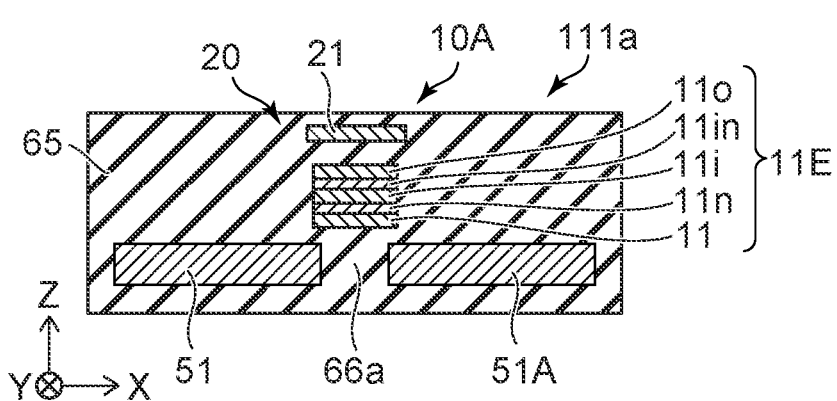
FIG. 6C

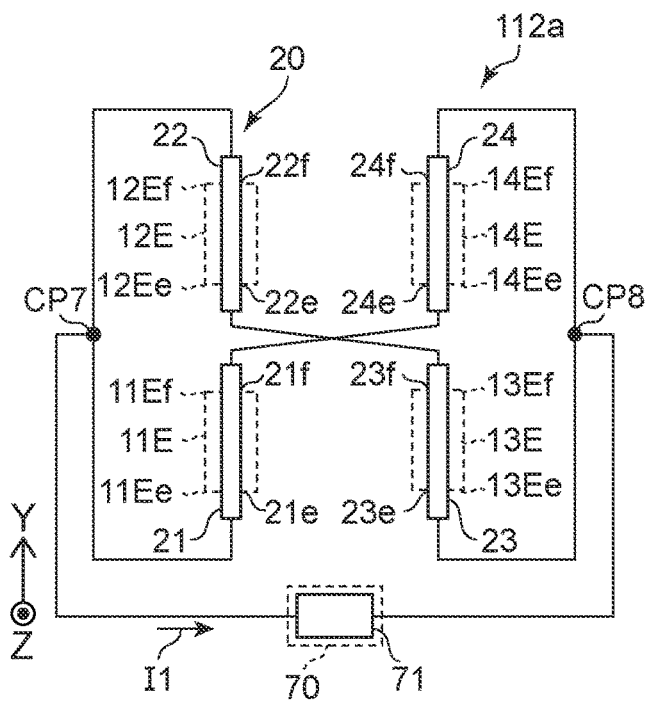
FIG. 14A
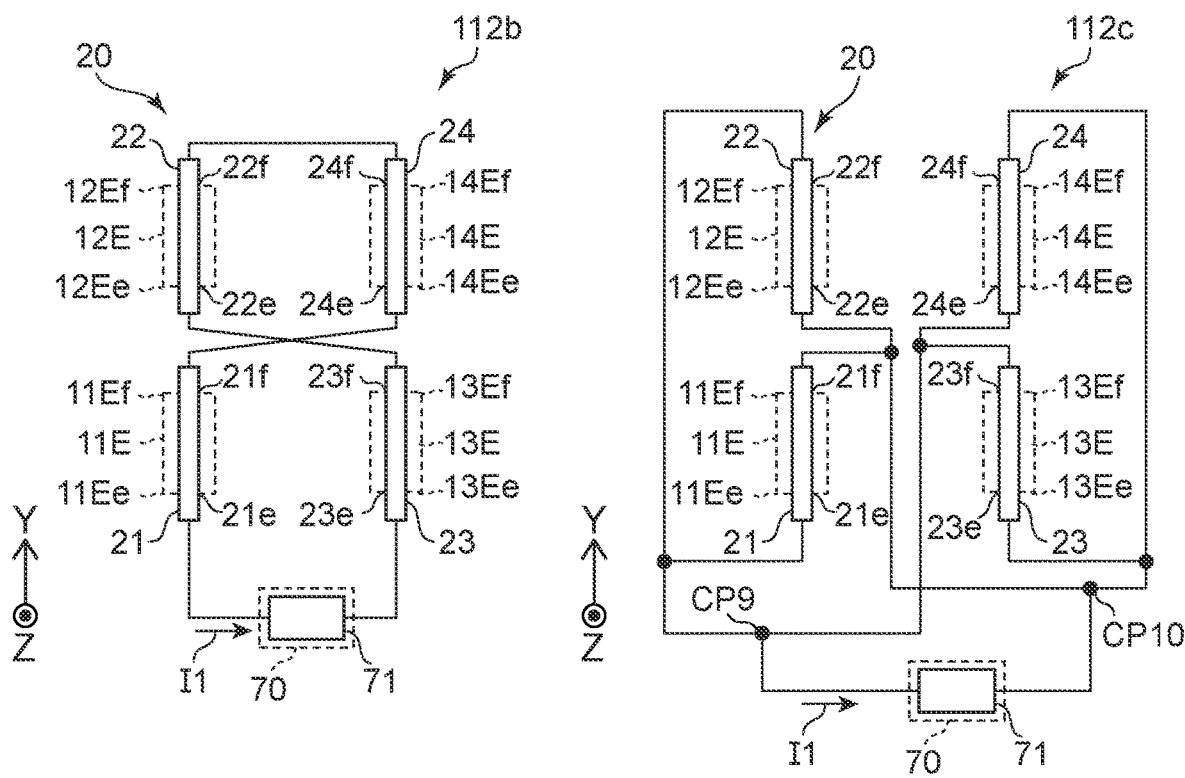
FIG. 14B
FIG. 14C

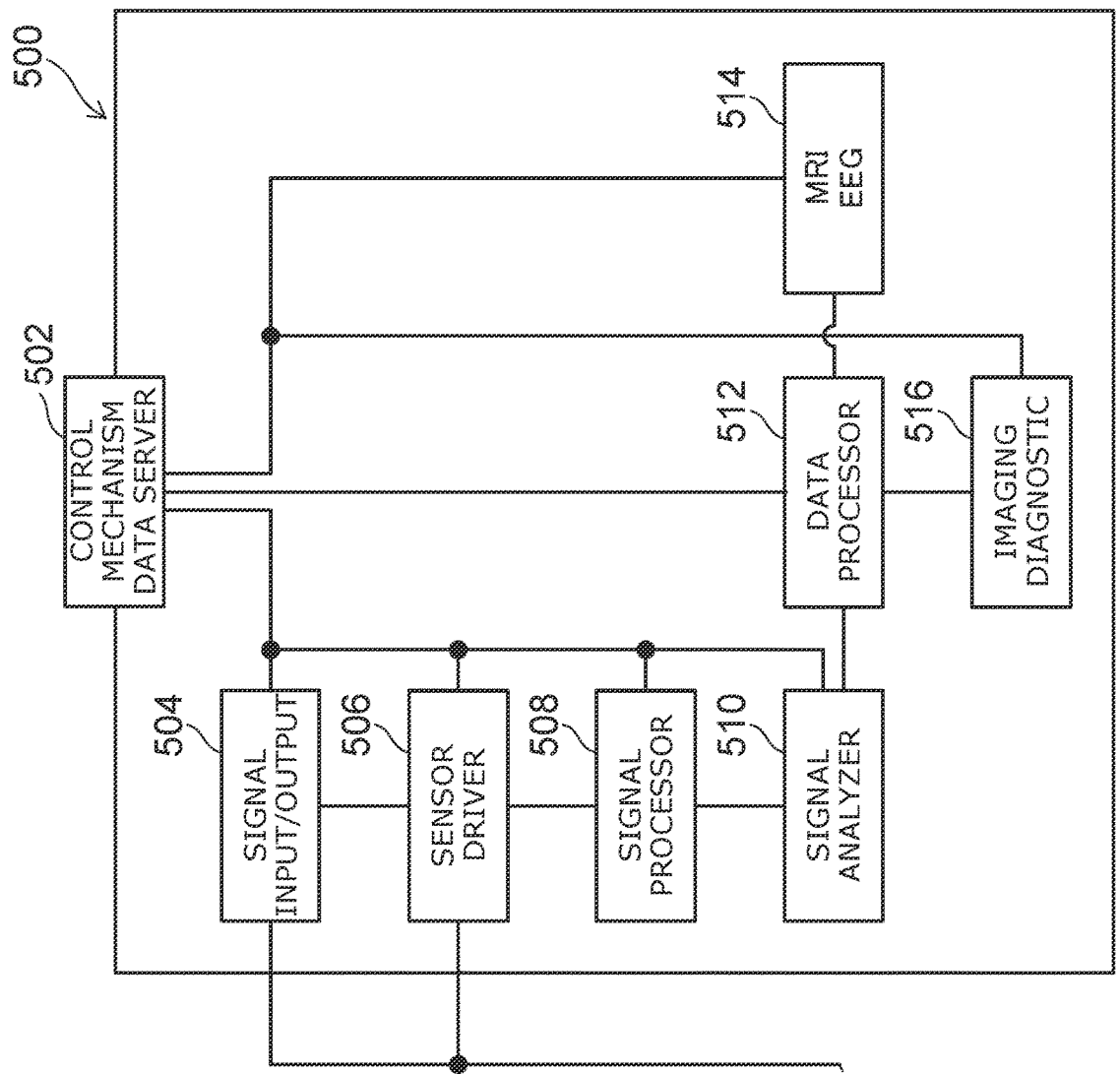
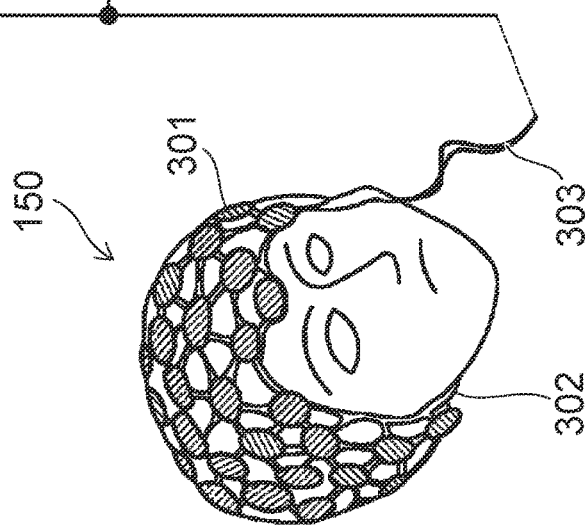
FIG. 21

MAGNETIC SENSOR AND INSPECTION DEVICE

CROSS-REFERENCE TO RELATED APPLICATIONS

This application is based upon and claims the benefit of priority from Japanese Patent Application No. 2021-010239, filed on Jan. 26, 2021; the entire contents of which are incorporated herein by reference.

FIELD

Embodiments described herein relate generally to a magnetic sensor and an inspection device.

BACKGROUND

There is a magnetic sensor that uses a magnetic layer. There is an inspection device that uses the magnetic sensor. It is desirable to increase the sensitivity of the magnetic sensor.

BRIEF DESCRIPTION OF THE DRAWINGS

FIGS. 5A to 5C are schematic views illustrating a magnetic sensor according to a second embodiment;

FIGS. 6A to 6C are schematic views illustrating a magnetic sensor according to the second embodiment;

FIGS. 14A to 14C are schematic views illustrating magnetic sensors according to the third embodiment;

FIG. 21 is a schematic view showing the magnetic sensor and the inspection device according to the fourth embodiment.

DETAILED DESCRIPTION

Figure 1A:
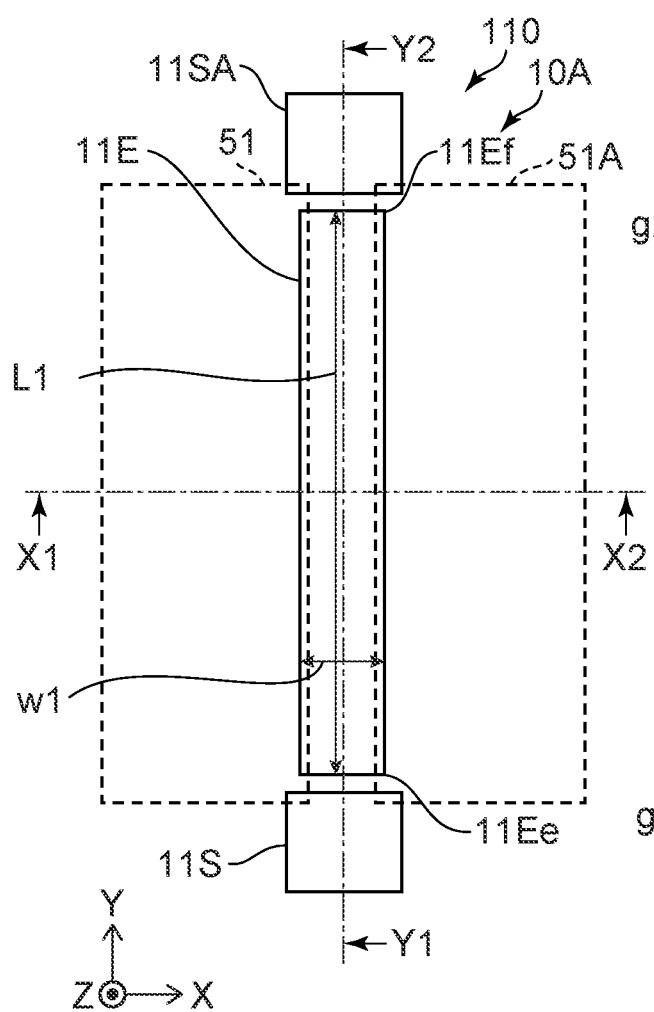
FIGS. 1A to 1C are schematic views illustrating a magnetic sensor according to a first embodiment.

According to one embodiment, a magnetic sensor includes a first sensor part, and a conductive member. The first sensor part includes a first magnetic element, a first side magnetic part, and a first counter side magnetic part. The conductive member includes a first corresponding portion along the first magnetic element. The first magnetic element includes a first magnetic layer, a first counter magnetic layer, a direction from the first magnetic layer toward the first counter magnetic layer being along a first direction, and a first intermediate magnetic layer located between the first magnetic layer and the first counter magnetic layer. The first side magnetic part includes a first side magnetic layer. The first counter side magnetic part includes a first counter side magnetic layer. The first intermediate magnetic layer is between the first side magnetic layer and the first counter side magnetic layer in a second direction crossing the first direction.

According to one embodiment, an inspection device includes the magnetic sensor described above, and a processor configured to process a signal output from the magnetic sensor.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

Exemplary embodiments will now be described with reference to the drawings.

The drawings are schematic or conceptual; and the relationships between the thickness and width of portions, the proportional coefficients of sizes among portions, etc., are not necessarily the same as the actual values thereof. Furthermore, the dimensions and proportional coefficients may be illustrated differently among drawings, even for identical portions.

In the specification of the application and the drawings, components similar to those described in regard to a drawing thereinabove are marked with like reference numerals, and a detailed description is omitted as appropriate.

First Embodiment

Figure 1B:
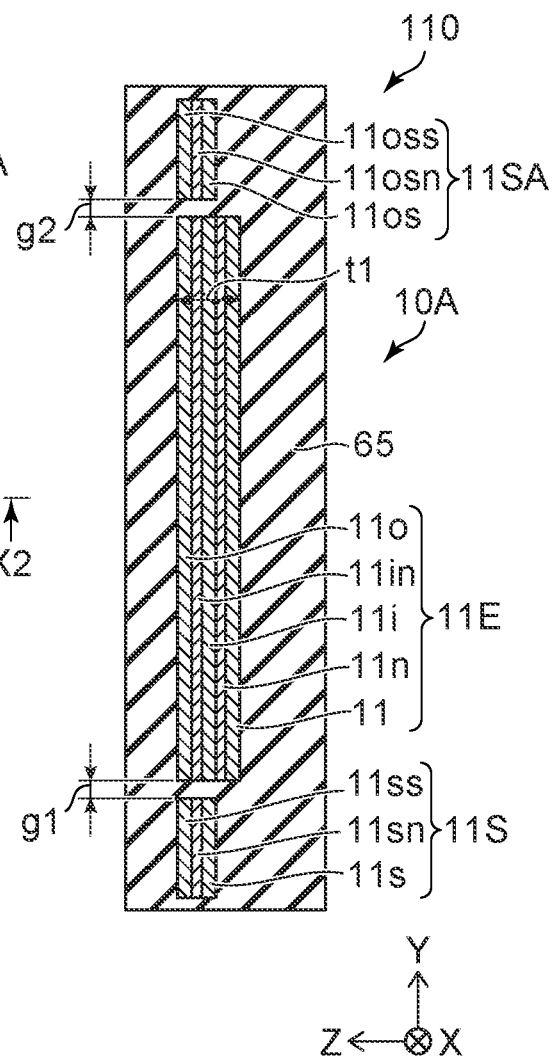
Figure 1C:
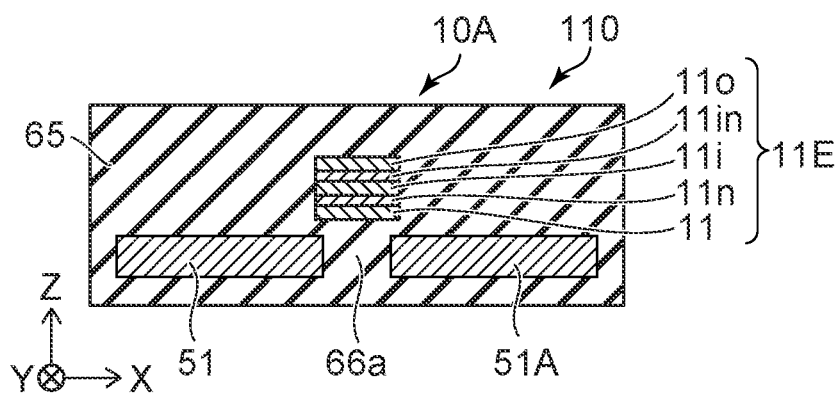

FIGS. 1A to 1C are schematic views illustrating a magnetic sensor according to a first embodiment. FIG. 1A is a plan view. FIG. 1B is a line Y1-Y2 cross-sectional view of FIG. 1A. FIG. 1C is a line X1-X2 cross-sectional view of FIG. 1A.

As shown in FIGS. 1A to 1C, the magnetic sensor 110 according to the embodiment includes a first sensor part 10A.

The first sensor part 10A includes a first magnetic element 11E, a first side magnetic part 11S, and a first counter side magnetic part 11SA.

As shown in FIGS. 1B and 1C, the first magnetic element 11E includes a first magnetic layer 11, a first counter magnetic layer 11O, and a first intermediate magnetic layer 11i. The direction from the first magnetic layer 11 toward the first counter magnetic layer 11O is along a first direction.

The first direction is taken as a Z-axis direction. One direction perpendicular to the Z-axis direction is taken as a Y-axis direction. A direction perpendicular to the Z-axis direction and the Y-axis direction is taken as an X-axis direction.

The first intermediate magnetic layer 11i is located between the first magnetic layer 11 and the first counter magnetic layer 11O.

In the example, the first magnetic element 11E includes a first nonmagnetic layer 11n and a first intermediate nonmagnetic layer 11in. The first nonmagnetic layer 11n is located between the first magnetic layer 11 and the first intermediate magnetic layer 11i. The first intermediate nonmagnetic layer 11in is located between the first intermediate magnetic layer 11i and the first counter magnetic layer 11O.

At least one of the first magnetic layer 11, the first counter magnetic layer 11O, or the first intermediate magnetic layer 11i includes, for example, at least one selected from the group consisting of Co, Fe, and Ni. These magnetic layers include, for example, at least one selected from the group consisting of CoFe, CoFeNi, and NiFe. These magnetic layers are, for example, ferromagnetic layers.

The first intermediate nonmagnetic layer 11in includes, for example, Ru. For example, the first intermediate magnetic layer 11i and the first counter magnetic layer 11O have antiferromagnetic coupling.

In one example, the first nonmagnetic layer 11n is conductive. The first nonmagnetic layer 11n includes, for example, at least one selected from the group consisting of Cu, Au, and Ag. For example, the first nonmagnetic layer 11n is a Cu layer. The first magnetic element 11E is, for example, a GMR (Giant Magnetic Resistance) element.

In another example, the first nonmagnetic layer 11n is insulative. The first nonmagnetic layer 11n includes, for example, MgO. In such a case, the first magnetic element 11E is, for example, a TMR (Tunnel Magneto Resistance) element.

As shown in FIG. 1B, the first side magnetic part 11S includes a first side magnetic layer 11s. The first counter side magnetic part 11SA includes a first counter side magnetic layer 11os. The first intermediate magnetic layer 11i is between the first side magnetic layer 11s and the first counter side magnetic layer 11os in a second direction that crosses the first direction. The second direction is, for example, the Y-axis direction.

In the example, the first side magnetic part 11S further includes a first stacked side magnetic layer 11ss. The first counter side magnetic part 11SA further includes a first counter stacked side magnetic layer 11oss. The first counter magnetic layer 11O is between the first stacked side magnetic layer 11ss and the first counter stacked side magnetic layer 11oss in the second direction (e.g., the Y-axis direction).

For example, the magnetization of the first intermediate magnetic layer 11i is made uniform by the first side magnetic layer 11s and the first counter side magnetic layer 11os. The magnetization of the first intermediate magnetic layer 11i stabilizes. For example, the magnetization of the end portion in the Y-axis direction of the first intermediate magnetic layer 11i is made uniform by the first side magnetic layer 11s and the first counter side magnetic layer 11os. The sensitivity of the magnetic sensor is improved by the magnetization of the first intermediate magnetic layer 11i stabilizing.

For example, the magnetization of the first counter magnetic layer 11O is made uniform by the first stacked side magnetic layer 11ss and the first counter stacked side magnetic layer 11oss. The magnetization of the first counter magnetic layer 11O stabilizes. For example, the magnetization of the end portion in the Y-axis direction of the first counter magnetic layer 11O is made uniform by the first stacked side magnetic layer 11ss and the first counter stacked side magnetic layer 11oss. For example, the magnetization of the first intermediate magnetic layer 11i is further stabilized by the magnetization of the first counter magnetic layer 11O stabilizing. According to the embodiment, a magnetic sensor can be provided in which the sensitivity can be increased.

As shown in FIG. 1B, the first side magnetic part 11S may further include a first side nonmagnetic layer 11sn. The first side nonmagnetic layer 11sn is located between the first side magnetic layer 11s and the first stacked side magnetic layer 11ss. As shown in FIG. 1B, the first counter side magnetic part 11SA may further include a first counter side nonmagnetic layer 11osn. The first counter side nonmagnetic layer 11osn is located between the first counter side magnetic layer 11os and the first counter stacked side magnetic layer 11oss. For example, the first side nonmagnetic layer 11sn and the first counter side nonmagnetic layer 11osn include a material that is included in the first intermediate nonmagnetic layer 11in.

An insulating member 65 may be located around the first magnetic element 11E, the first side magnetic part 11S, and the first counter side magnetic part 11SA.

According to the embodiment, a portion of the insulating member 65 may be located between the first side magnetic layer 11s and the first stacked side magnetic layer 11ss and between the first counter side magnetic layer 11os and the first counter stacked side magnetic layer 11oss.

As shown in FIG. 1A, the length along the second direction (the Y-axis direction) of the first magnetic element 11E is taken as a first length L1. The first magnetic element 11E includes a first end portion 11Ee and a first other-end portion 11Ef. The direction from the first end portion 11Ee toward the first other-end portion 11Ef is along the second direction (e.g., the Y-axis direction). The first end portion 11Ee and the first other-end portion 11Ef correspond to two end portions in the Y-axis direction of the first magnetic element 11E.

As shown in FIG. 1A, the length along a third direction of the first magnetic element 11E is taken as a first width w1. The third direction crosses a plane that includes the first and second directions. The third direction is, for example, the X-axis direction. According to the embodiment, the first length L1 is greater than the first width w1. For example, the magnetization of the magnetic layer included in the first magnetic element 11E is along the Y-axis direction. For example, the first length L1 is not less than 10 times and not more than 100 times the first width w1.

For example, the magnetization of the first counter magnetic layer 11O has one of a first orientation or a second orientation. For example, the magnetization of the first intermediate magnetic layer 11i has the other of the first orientation or the second orientation. The first orientation is from the first end portion 11Ee toward the first other-end portion 11Ef. The second orientation is from the first other-end portion 11Ef toward the first end portion 11Ee.

For example, the magnetization of the first side magnetic layer 11s and the magnetization of the first counter side magnetic layer 11os have the same orientation as the magnetization of the first intermediate magnetic layer 11i. For example, the magnetization of the first stacked side magnetic layer 11ss and the magnetization of the first counter stacked side magnetic layer 11oss have the same orientation as the magnetization of the first counter magnetic layer 11O.

As shown in FIG. 1B, the length along the first direction (the Z-axis direction) of the first magnetic element 11E is taken as a first thickness t1. The first length L1 is greater than the first thickness t1.

As shown in FIG. 1B, the distance along the second direction (the Y-axis direction) between the first side magnetic part 11S and the first magnetic element 11E is taken as a distance g1. The distance g1 is, for example, not more than 0.01 times the first length L1. Because the distance g1 is not more than 0.01 times the first length L1, for example, the stabilization of the magnetization of the magnetic layer included in the first magnetic element 11E by the first side magnetic part 11S is effectively obtained. Because the distance g1 is not less than 0.001 times the first length L1, the electrical insulation between the first side magnetic part 11S and the first magnetic element 11E is stabilized.

As shown in FIG. 1B, the distance along the second direction (the Y-axis direction) between the first counter side magnetic part 11SA and the first magnetic element 11E is taken as a distance g2. The distance g2 is, for example, not more than 0.01 times the first length L1. Because the distance g2 is not more than 0.01 times the first length L1, for example, the stabilization of the magnetization of the magnetic layer included in the first magnetic element 11E by the first counter side magnetic part 11SA is effectively obtained. Because the distance g2 is not less than 0.001 times the first length L1, the electrical insulation between the first counter side magnetic part 11SA and the first magnetic element 11E is stabilized.

In the example as shown in FIGS. 1A and 1C, the first sensor part 10A further includes a first magnetic member 51 and a first counter magnetic member 51A. The direction from the first magnetic member 51 toward the first counter magnetic member 51A is along the third direction. The third direction crosses a plane that includes the first and second directions. The third direction is, for example, the X-axis direction.

As shown in FIG. 1C, the first magnetic element 11E overlaps a region 66a between the first magnetic member 51 and the first counter magnetic member 51A in the first direction (the Z-axis direction). The region 66a may be, for example, a portion of the insulating member 65.

As shown in FIG. 1C, for example, a portion of the first magnetic element 11E overlaps a portion of the first magnetic member 51 in the first direction (the Z-axis direction). Another portion of the first magnetic element 11E overlaps a portion of the first counter magnetic member 51A in the first direction.

The magnetic field of the detection object is concentrated by the first magnetic member 51 and the first counter magnetic member 51A. The concentrated magnetic field is efficiently applied to the first magnetic element 11E. Higher sensitivity is obtained thereby. For example, the first magnetic member 51 and the first counter magnetic member 51A function as MFCs (Magnetic Field Concentrators).

Figure 2:
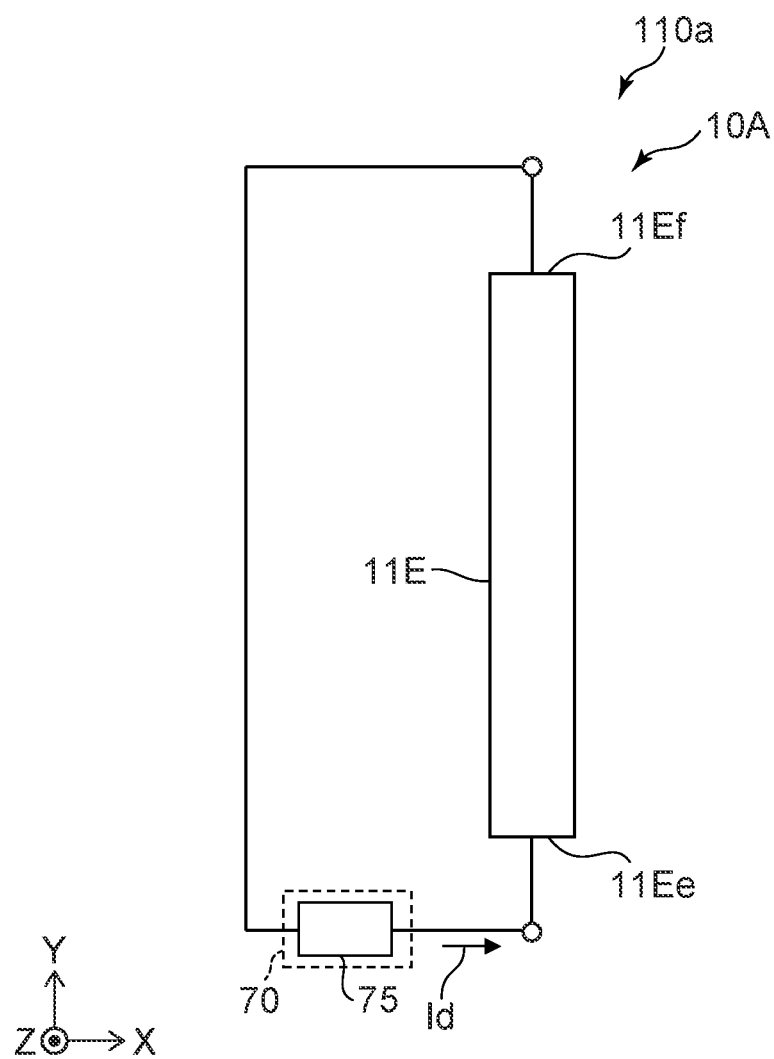
FIG. 2 is a schematic view illustrating a magnetic sensor according to the first embodiment.

FIG. 2 is a schematic view illustrating a magnetic sensor according to the first embodiment.

As shown in FIG. 2, the magnetic sensor 110a may include an element current circuit 75. The element current circuit 75 is configured to supply an element current Id to the first magnetic element 11E. For example, the element current circuit 75 is configured to supply the element current Id between the first end portion 11Ee and the first other-end portion 11Ef of the first magnetic element 11E. For example, the element current circuit 75 is included in a circuit part 70. The circuit part 70 may be configured to detect the electrical resistance of the first magnetic element 11E based on the element current Id. The electrical resistance of the first magnetic element 11E changes according to the magnetic field of a detection object. For example, the orientation of the magnetization of the first magnetic layer 11 changes according to the magnetic field of the detection object. For example, the first magnetic layer 11 is a free magnetic layer.

Figure 3A:
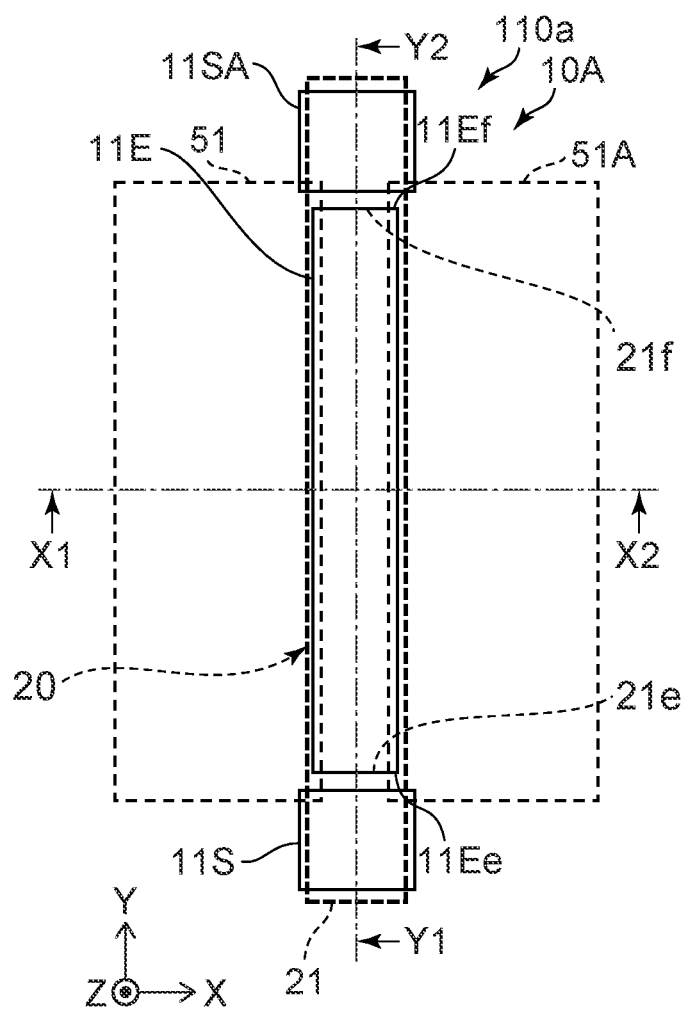
FIGS. 3A to 3C are schematic views illustrating the magnetic sensor according to the first embodiment.
Figure 3B:
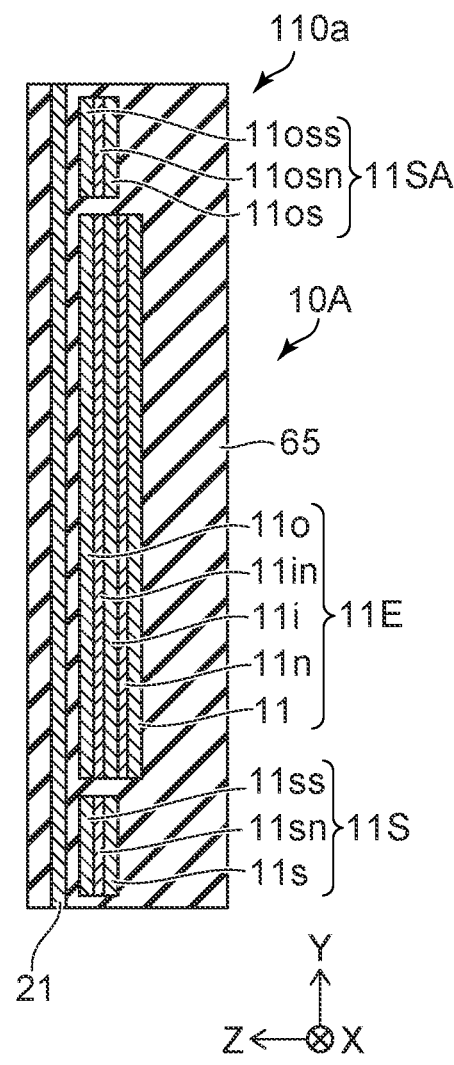
Figure 3C:
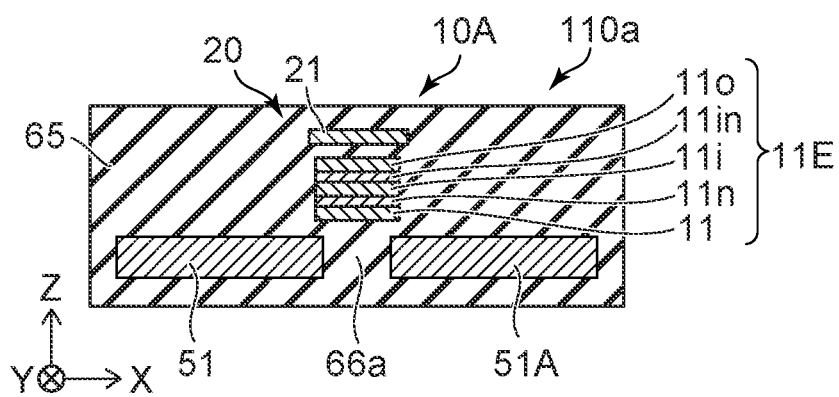

FIGS. 3A to 3C are schematic views illustrating the magnetic sensor according to the first embodiment. FIG. 3A is a plan view. FIG. 3B is a line Y1-Y2 cross-sectional view of FIG. 3A. FIG. 3C is a line X1-X2 cross-sectional view of FIG. 3A.

As shown in FIGS. 3A and 3C, the magnetic sensor 110a according to the embodiment includes a conductive member 20. Otherwise, the configuration of the magnetic sensor 110a may be similar to the configuration of the magnetic sensor 110.

In the magnetic sensor 110a, the conductive member 20 includes a first corresponding portion 21. The first corresponding portion 21 is along the first magnetic element 11E. For example, the first corresponding portion 21 overlaps the first magnetic element 11E in a direction that crosses the second direction (the Y-axis direction). For example, the first corresponding portion 21 overlaps the first magnetic element 11E in the Z-axis direction. The positions in the Z-axis direction of the first magnetic element 11E, the first corresponding portion 21, the first magnetic member 51, and the first counter magnetic member 51A are arbitrary. A magnetic field (a current magnetic field) that is based on a current supplied to the first corresponding portion 21 is applied to the first magnetic element 11E. By using a current magnetic field of an alternating current as described below, it is possible to suppress noise and detect with higher sensitivity.

Figure 4:
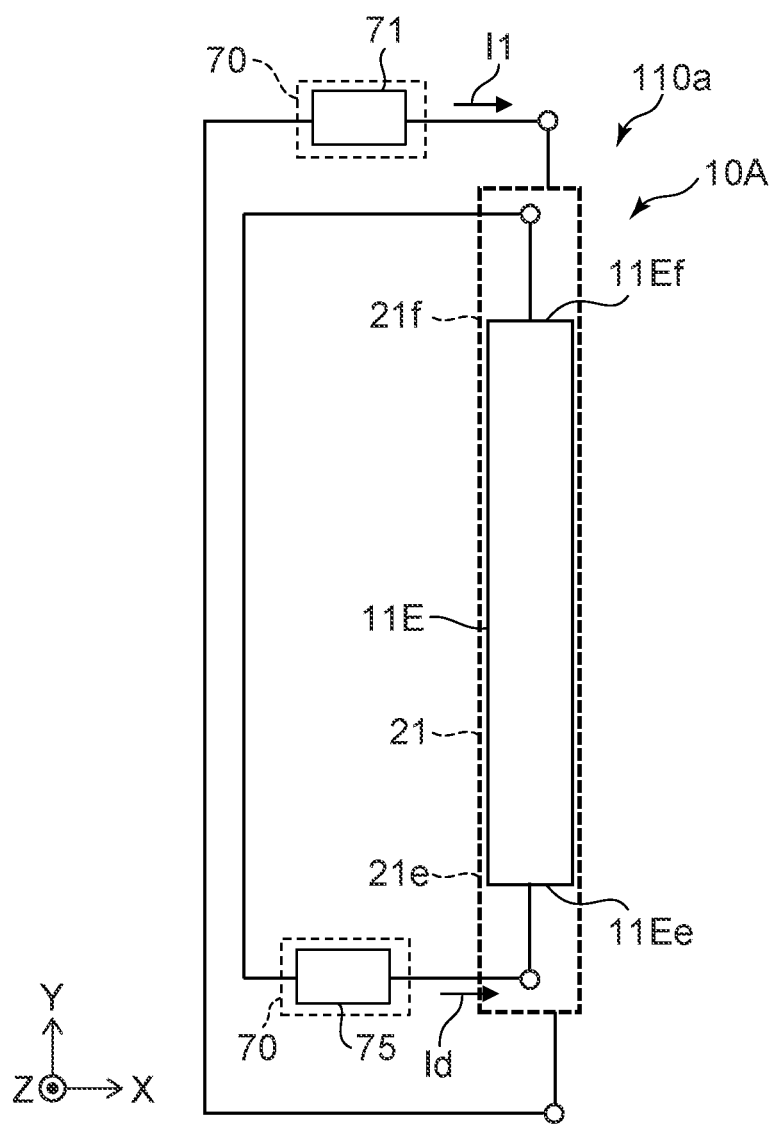
FIG. 4 is a schematic view illustrating the magnetic sensor according to the first embodiment.

FIG. 4 is a schematic view illustrating the magnetic sensor according to the first embodiment.

As shown in FIG. 4, the first magnetic element 11E includes the first end portion 11Ee and the first other-end portion 11Ef as described above. The direction from the first end portion 11Ee toward the first other-end portion 11Ef is along the second direction (the Y-axis direction). The first corresponding portion 21 includes a first portion 21e and a first other-portion 21f. The first portion 21e corresponds to the first end portion 11Ee. The first other-portion 21f corresponds to the first other-end portion 11Ef. For example, the first portion 21e overlaps the first end portion 11Ee in the first direction (the Z-axis direction). For example, the first other-portion 21f overlaps the first other-end portion 11Ef in the first direction.

The magnetic sensor 110a may include the element current circuit 75 and a first current circuit 71. As described above, the element current circuit 75 is configured to supply the element current Id between the first end portion 11Ee and the first other-end portion 11Ef of the first magnetic element 11E. The first current circuit 71 is configured to supply a first current I1 that includes an alternating current component to the first corresponding portion 21. The first current circuit 71 is configured to supply the first current I1 between the first portion 21e and the first other-portion 21f. The first current circuit 71 may be included in the circuit part 70. An example of the detection using the first current I1 that includes the alternating current component is described below.

Second Embodiment

FIGS. 5A to 5C are schematic views illustrating a magnetic sensor according to a second embodiment. FIG. 5A is a plan view. FIG. 5B is a line Y1-Y2 cross-sectional view of FIG. 5A. FIG. 5C is a line X1-X2 cross-sectional view of FIG. 5A.

As shown in FIGS. 5A to 5C, the magnetic sensor 111 according to the embodiment includes the sensor part 10A.

In the magnetic sensor 111 as shown in FIGS. 5A and 5B, the first sensor part 10A includes the first magnetic element 11E, a first stacked magnetic layer 11sL, and a first counter stacked magnetic layer 11osL. The first stacked magnetic layer 11sL and the first counter stacked magnetic layer 11osL include, for example, at least one selected from the group consisting of IrMn and PtMn.

The first magnetic element 11E includes the first magnetic layer 11, the first counter magnetic layer 11o, the first intermediate magnetic layer 11i, the first nonmagnetic layer 11n, and the first intermediate nonmagnetic layer 11in. The direction from the first magnetic layer 11 toward the first counter magnetic layer 11o is along the first direction (the Z-axis direction). The first intermediate magnetic layer 11i is located between the first magnetic layer 11 and the first counter magnetic layer 11o. The first nonmagnetic layer 11n is located between the first magnetic layer 11 and the first intermediate magnetic layer 11i. The first intermediate nonmagnetic layer 11in is located between the first intermediate magnetic layer 11i and the first counter magnetic layer 11o.

The direction from the first stacked magnetic layer 11sL toward the first counter stacked magnetic layer 11osL is along the second direction that crosses the first direction. The second direction is, for example, the Y-axis direction. A portion 11op of the first counter magnetic layer 11o is between the first magnetic layer 11 and the first stacked magnetic layer 11sL. For example, the portion 11op of the first counter magnetic layer 11o is between the first intermediate nonmagnetic layer 11in and the first stacked magnetic layer 11sL. Another portion 11oq of the first counter magnetic layer 11o is between the first magnetic layer 11 and the first counter stacked magnetic layer 11osL. For example, the other portion 11oq of the first counter magnetic layer 11o is between the first intermediate nonmagnetic layer 11in and the first counter stacked magnetic layer 11osL.

For example, the magnetization of the first counter magnetic layer 11o is made uniform by the first stacked magnetic layer 11sL and the first counter stacked magnetic layer 11osL. For example, the magnetization at the end portion in the Y-axis direction of the first counter magnetic layer 11o is controlled by the first stacked magnetic layer 11sL and the first counter stacked magnetic layer 11osL. By making the magnetization of the first counter magnetic layer 11o uniform, for example, the magnetization of the first intermediate magnetic layer 11i is made uniform. A magnetic sensor can be provided in which the sensitivity can be increased.

For example, the first stacked magnetic layer 11sL may contact the portion 11op of the first counter magnetic layer 11o. Or, the distance along the first direction (the Z-axis direction) between the first stacked magnetic layer 11sL and the portion 11op of the first counter magnetic layer 11o is, for example, not more than 0.1 times the thickness of the first counter magnetic layer 11o. The thickness of the first counter magnetic layer 11o is the length along the first direction (the Z-axis direction) of the first counter magnetic layer 11o. For example, the first counter stacked magnetic layer 11osL contacts the other portion 11oq of the first counter magnetic layer 11o. Or, the distance along the first direction between the first counter stacked magnetic layer 11osL and the other portion 11oq of the first counter magnetic layer 11o is not more than 0.1 times the thickness of the first counter magnetic layer 11o. Thereby, the magnetization of the first counter magnetic layer 11o is easily stabilized by the first stacked magnetic layer 11sL and the first counter stacked magnetic layer 11osL.

As shown in FIG. 5A, the length along the second direction (the Y-axis direction) of the first stacked magnetic layer 11sL is taken as a length La1. The length La1 is, for example, not less than 0.01 times and not more than 0.1 times the length (the first length L1) along the second direction of the first magnetic element 11E. The length along the second direction of the first counter stacked magnetic layer 11osL is taken as a length Lb1. The length Lb1 is, for example, not less than 0.01 times and not more than 0.1 times the length (the first length L1) along the second direction of the first magnetic element 11E. For example, the magnetization of the first counter magnetic layer 11o is favorably controlled by such a length La1 and such a length Lb1.

The configuration and materials of the magnetic sensor 110 described above are applicable to the magnetic sensor 111. For example, the magnetic sensor 111 may include the first magnetic member 51 and the first counter magnetic member 51A. According to the second embodiment as described below, the conductive member 20 described with reference to the magnetic sensor 110a may be included.

FIGS. 6A to 6C are schematic views illustrating a magnetic sensor according to the second embodiment. FIG. 6A is a plan view. FIG. 6B is a line Y1-Y2 cross-sectional view of FIG. 6A. FIG. 6C is a line X1-X2 cross-sectional view of FIG. 6A.

As shown in FIGS. 6A and 6C, the magnetic sensor 111a according to the embodiment includes the conductive member 20. Otherwise, the configuration of the magnetic sensor 111a may be similar to the configuration of the magnetic sensor 111.

In the magnetic sensor 111a, the conductive member 20 includes the first corresponding portion 21. The first corresponding portion 21 is along the first magnetic element 11E. For example, the first corresponding portion 21 overlaps the first magnetic element 11E in a direction that crosses the second direction (the Y-axis direction). For example, the first corresponding portion 21 overlaps the first magnetic element 11E in the Z-axis direction. The positions in the Z-axis direction of the first magnetic element 11E, the first corresponding portion 21, the first magnetic member 51, and the first counter magnetic member 51A are arbitrary. A magnetic field (a current magnetic field) that is based on a current supplied to the first corresponding portion 21 is applied to the first magnetic element 11E. As described below, for example, by using a current magnetic field of an alternating current, it is possible to suppress noise and detect with higher sensitivity.

The magnetic sensor 111a also may include the element current circuit 75 and the first current circuit 71 (referring to FIG. 4). As described above, the element current circuit 75 is configured to supply the element current Id between the first end portion 11Ee and the first other-end portion 11Ef of the first magnetic element 11E. The first current circuit 71 is configured to supply the first current I1 that includes the alternating current component to the first corresponding portion 21. The first current circuit 71 is configured to supply the first current I1 between the first portion 21e and the first other-portion 21f. As described below, the electrical resistance of the first magnetic element 11E has an even-function characteristic. It is possible to detect with suppressed noise by using the even-function electrical resistance and the first current I1 that includes the alternating current component.

An example of characteristics of the first magnetic element 11E will now be described. The following description is applicable to the magnetic sensors according to the first and second embodiments.

Figure 7A:
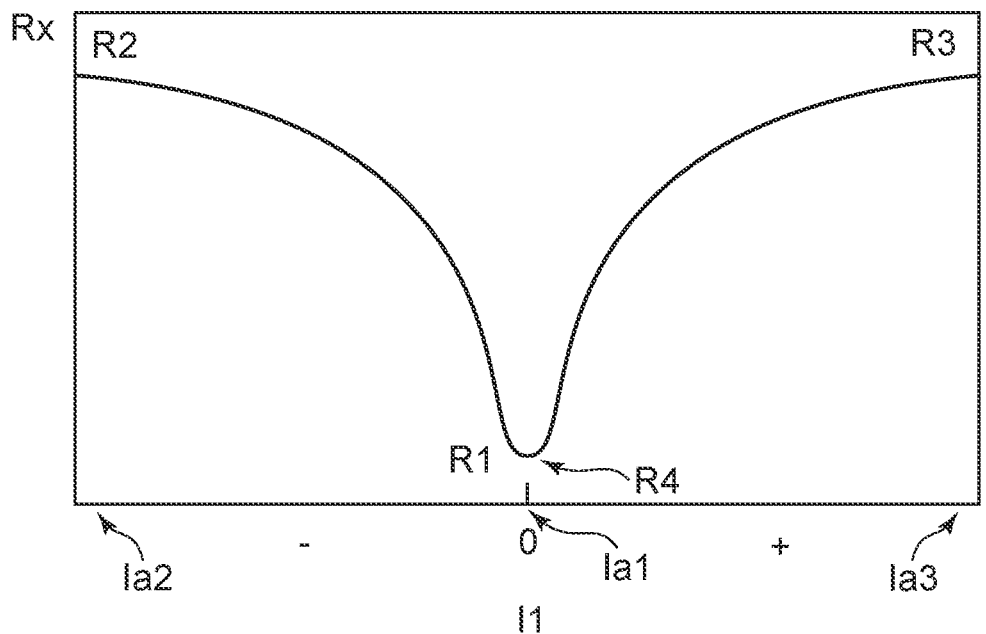
FIGS. 7A and 7B are schematic views illustrating characteristics of the magnetic sensor according to the embodiment.
Figure 7B:
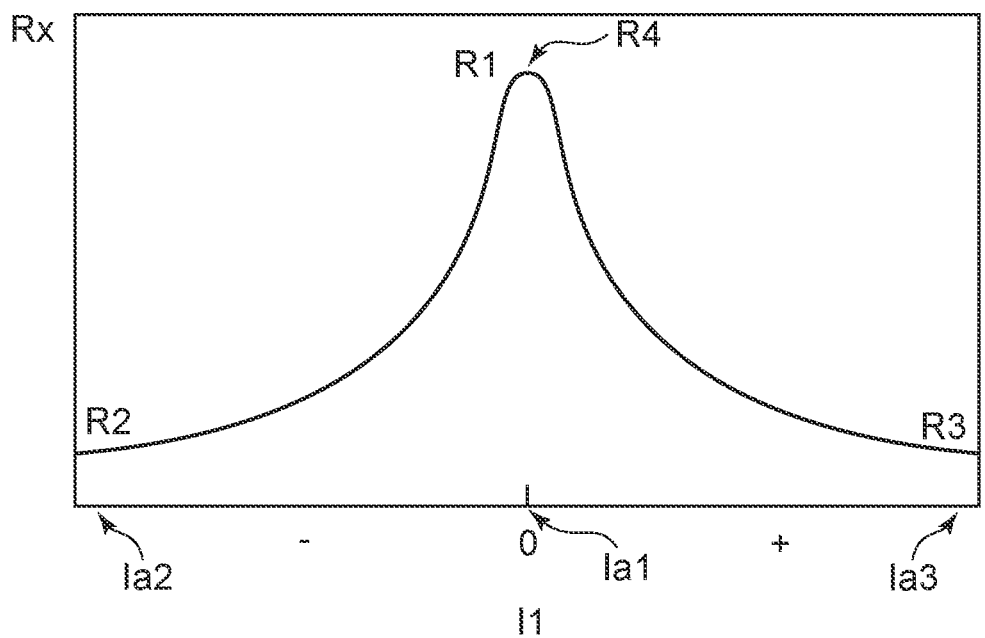

FIGS. 7A and 7B are schematic views illustrating characteristics of the magnetic sensor according to the embodiment.

In these figures, the horizontal axis corresponds to the value of the current (e.g., the first current I1) flowing in the conductive member 20 (e.g., the first corresponding portion 21). The vertical axis is an electrical resistance Rx of the first magnetic element 11E. According to the embodiment as shown in FIGS. 7A and 7B, the electrical resistance Rx has an even-function characteristic with respect to the change of the current (the first current I1).

For example, the electrical resistance Rx of the first magnetic element 11E has a first value R1 when a first-value current Ia1 is supplied to the first corresponding portion 21. The electrical resistance Rx has a second value R2 when a second-value current Ia2 is supplied to the first corresponding portion 21. The electrical resistance Rx has a third value R3 when a third-value current Ia3 is supplied to the first corresponding portion 21. The absolute value of the first-value current Ia1 is less than the absolute value of the second-value current Ia2 and less than the absolute value of the third-value current Ia3. For example, the first-value current Ia1 may be substantially 0. The orientation of the second-value current Ia2 is opposite to the orientation of the third-value current Ia3.

In the example of FIG. 7A, the first value R1 is less than the second value R2 and less than the third value R3. In the example of FIG. 7B, the first value R1 is greater than the second value R2 and greater than the third value R3.

For example, the electrical resistance Rx has a fourth value R4 when a current does not flow in the first corresponding portion 21. For example, the first value R1 is substantially equal to the fourth value R4 when the current does not flow. For example, the ratio of the absolute value of the difference between the first value R1 and the fourth value R4 to the fourth value R4 is not more than 0.01. The ratio may be not more than 0.001. A substantially even-function characteristic is obtained for the positive and negative currents.

Such a relationship between the first current I1 and the electrical resistance Rx is based on the magnetic field due to the first current I1 being applied to the first magnetic element 11E and based on the electrical resistance Rx of the first magnetic element 11E changing according to the intensity of the magnetic field.

Similarly to the example shown in FIG. 7A or FIG. 7B, the electrical resistance Rx also has an even-function characteristic when an external magnetic field is applied to the first magnetic element 11E. The external magnetic field includes, for example, a component along the X-axis direction.

Figure 8A:
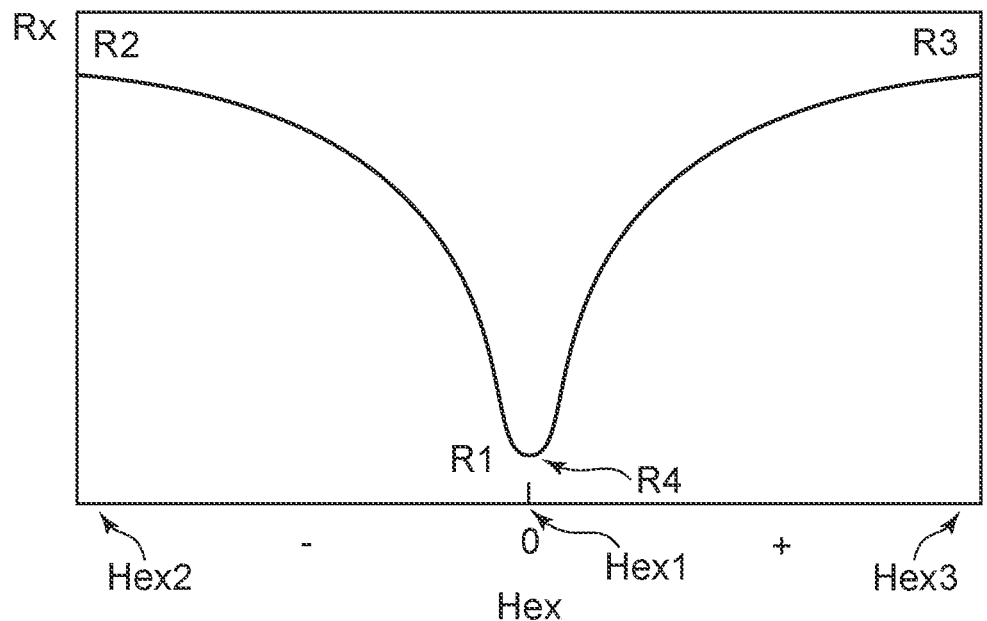
FIGS. 8A and 8B are schematic views illustrating characteristics of the magnetic sensor according to the embodiment.
Figure 8B:
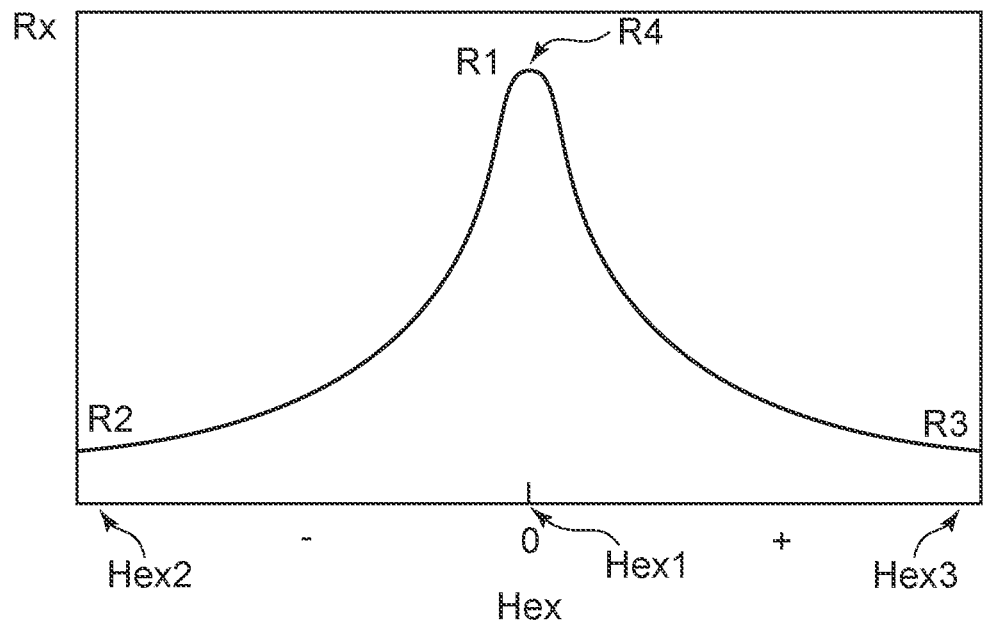

FIGS. 8A and 8B are schematic views illustrating characteristics of the magnetic sensor according to the embodiment.

In these figures, the horizontal axis is the intensity of an external magnetic field Hex that is applied to the first magnetic element 11E. The vertical axis is the electrical resistance Rx of the first magnetic element 11E. These figures correspond to the R-H characteristic. As shown in FIGS. 8A and 8B, the electrical resistance Rx has an even-function characteristic with respect to the external magnetic field Hex applied to the first magnetic element 11E. The external magnetic field Hex includes, for example, an X-axis direction component.

As shown in FIGS. 8A and 8B, the electrical resistance Rx of the first magnetic element 11E has the first value R1 when a first magnetic field Hex1 is applied to the first magnetic element 11E. The electrical resistance Rx has the second value R2 when a second magnetic field Hex2 is applied to the first magnetic element 11E. The electrical resistance Rx has the third value R3 when a third magnetic field Hex3 is applied to the first magnetic element 11E. The absolute value of the first magnetic field Hex1 is less than the absolute value of the second magnetic field Hex2 and less than the absolute value of the third magnetic field Hex3. The orientation of the second magnetic field Hex2 is opposite to the orientation of the third magnetic field Hex3.

In the example of FIG. 8A, the first value R1 is less than the second value R2 and less than the third value R3. In the example of FIG. 8B, the first value R1 is greater than the second value R2 and greater than the third value R3. For example, the electrical resistance Rx has the fourth value R4 when the external magnetic field is not applied to the first magnetic element 11E. The first value R1 is substantially equal to the fourth value R4 when the external magnetic field is not applied. For example, the ratio of the absolute value of the difference between the first value R1 and the fourth value R4 to the fourth value R4 is not more than 0.01. The ratio may be not more than 0.001. A substantially even-function characteristic is obtained for the positive and negative external magnetic fields.

By utilizing such an even-function characteristic, highly-sensitive detection is possible as follows.

An example will now be described in which the first current I1 is an alternating current and substantially does not include a direct current component. The first current I1 (the alternating current) is supplied to the first corresponding portion 21; and an alternating magnetic field due to the alternating current is applied to the first magnetic element 11E. An example of the change of the electrical resistance Rx at this time will be described.

Figure 9A:
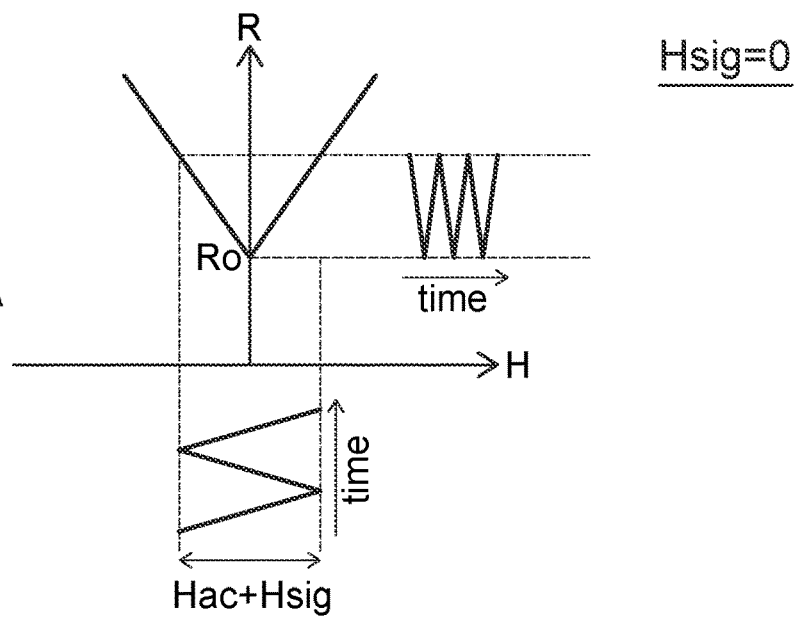
FIGS. 9A to 9C are graphs illustrating characteristics of the magnetic sensor according to the embodiment.
Figure 9B:
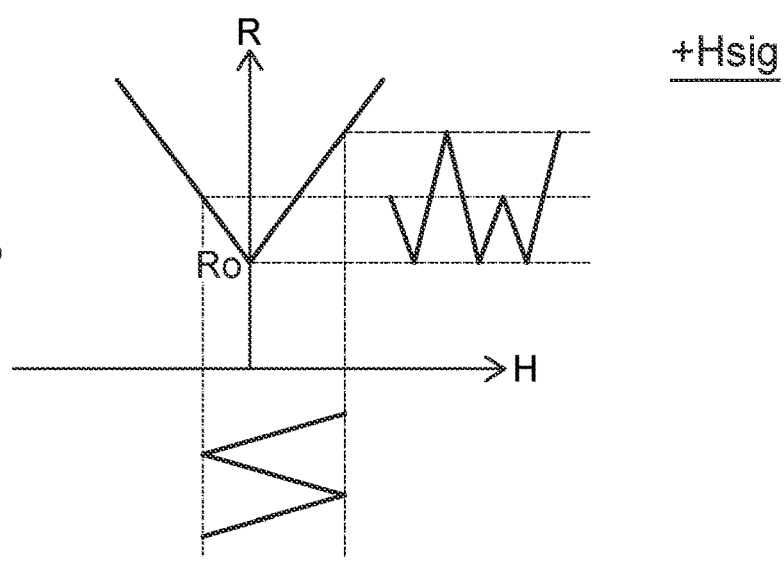
Figure 9C:
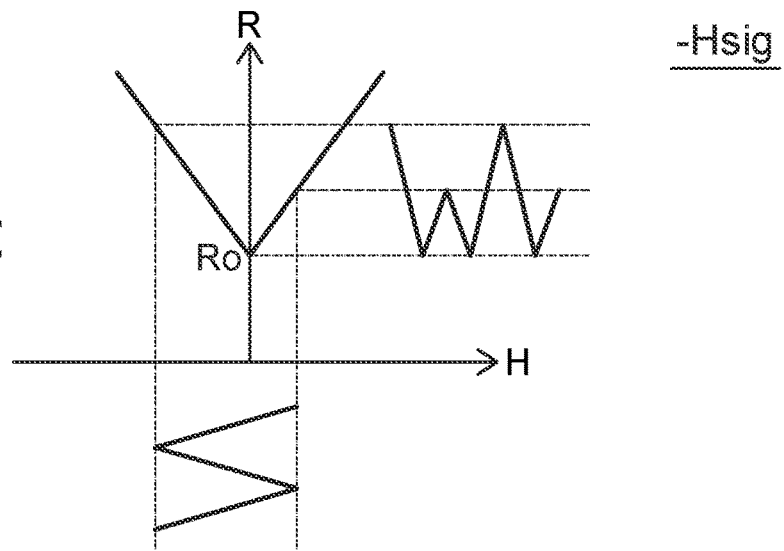

FIGS. 9A to 9C are graphs illustrating characteristics of the magnetic sensor according to the embodiment.

FIG. 9A shows characteristics when a signal magnetic field Hsig (an external magnetic field) applied to the first magnetic element 11E is 0. FIG. 9B shows characteristics when the signal magnetic field Hsig is positive. FIG. 9C shows characteristics when the signal magnetic field Hsig is negative. These figures show the relationship between a magnetic field H and a resistance R (corresponding to the electrical resistance Rx).

As shown in FIG. 9A, when the signal magnetic field Hsig is 0, the resistance R has a characteristic that is symmetric with respect to the positive and negative magnetic field H. In the example, when an alternating magnetic field Hac is zero, the resistance R is a low resistance Ro. For example, the magnetization of the free magnetic layer is rotated substantially identically to the positive and negative magnetic field H. Therefore, a symmetric resistance change is obtained. The change of the resistance R with respect to the alternating magnetic field Hac has the same value between the positive and negative polarities. The period of the change of the resistance R is ½ times the period of the alternating magnetic field Hac. The change of the resistance R substantially does not include the frequency component of the alternating magnetic field Hac.

As shown in FIG. 9B, the characteristic of the resistance R shifts to the positive magnetic field H side when a positive signal magnetic field Hsig is applied. For example, the resistance R becomes high for the alternating magnetic field Hac on the positive side. The resistance R becomes low for the alternating magnetic field Hac on the negative side.

As shown in FIG. 9C, the characteristic of the resistance R shifts to the negative magnetic field H side when a negative signal magnetic field Hsig is applied. For example, the resistance R becomes low for the alternating magnetic field Hac on the positive side. The resistance R becomes high for the alternating magnetic field Hac on the negative side.

Change in the resistance R is different for the positive and negative of the alternating magnetic field Hac when a signal magnetic field Hsig with non-zero magnitude is applied. The period of the change of the resistance R with respect to the positive and negative of the alternating magnetic field Hac is equal to the period of the alternating magnetic field Hac. An output voltage that has an alternating current frequency component corresponding to the signal magnetic field Hsig is generated.

The characteristics described above are obtained in the case where the signal magnetic field Hsig does not temporally change. The case where the signal magnetic field Hsig temporally changes is as follows. The frequency of the signal magnetic field Hsig is taken as a signal frequency fsig. The frequency of the alternating magnetic field Hac is taken as an alternating current frequency fac. In such a case, an output that corresponds to the signal magnetic field Hsig is generated at the frequency of fac±fsig.

In the case where the signal magnetic field Hsig temporally changes, the signal frequency fsig is, for example, not more than 1 kHz. On the other hand, the alternating current frequency fac is sufficiently greater than the signal frequency fsig. For example, the alternating current frequency fac is not less than 10 times the signal frequency fsig.

For example, the signal magnetic field Hsig can be detected with high accuracy by extracting an output voltage having the same period (frequency) component (alternating current frequency component) as the period (the frequency) of the alternating magnetic field Hac. In the magnetic sensor according to the embodiment, the external magnetic field Hex (the signal magnetic field Hsig) that is the detection object can be detected with high sensitivity by utilizing such characteristics. According to the embodiment, the external magnetic field Hex (the signal magnetic field Hsig) and the alternating magnetic field Hac due to the first current I1 can be efficiently applied to the first magnetic element 11E by the magnetic member 51. High sensitivity is obtained.

Third Embodiment

According to a third embodiment, the magnetic sensor includes multiple magnetic elements.

Figure 10:
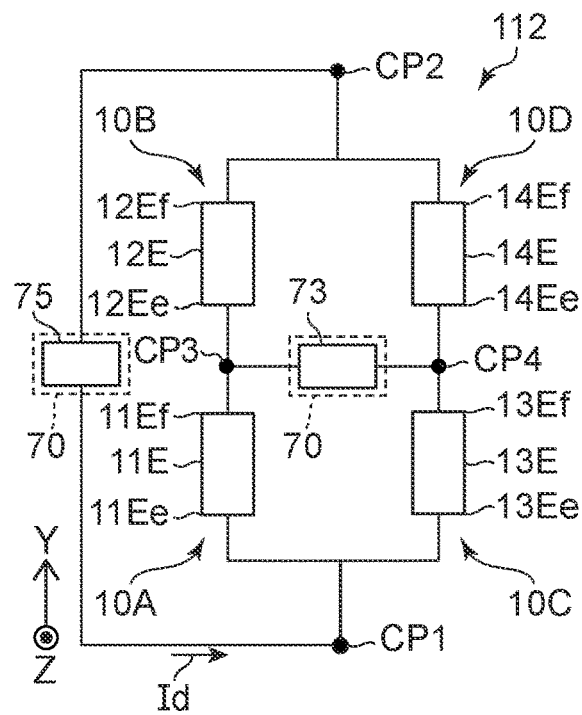
FIG. 10 is a schematic view illustrating a magnetic sensor according to a third embodiment.
Figure 11:
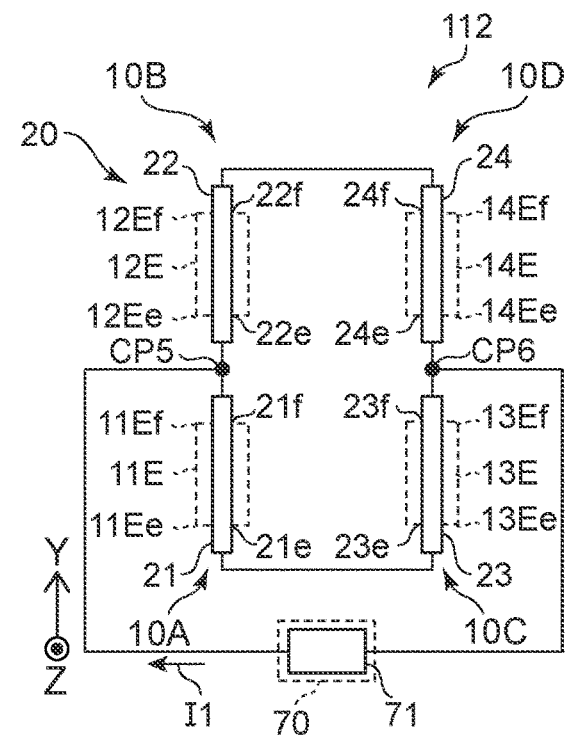
FIG. 11 is a schematic view illustrating the magnetic sensor according to the third embodiment.

FIGS. 10 and 11 are schematic views illustrating the magnetic sensor according to the third embodiment.

Figure 12A:
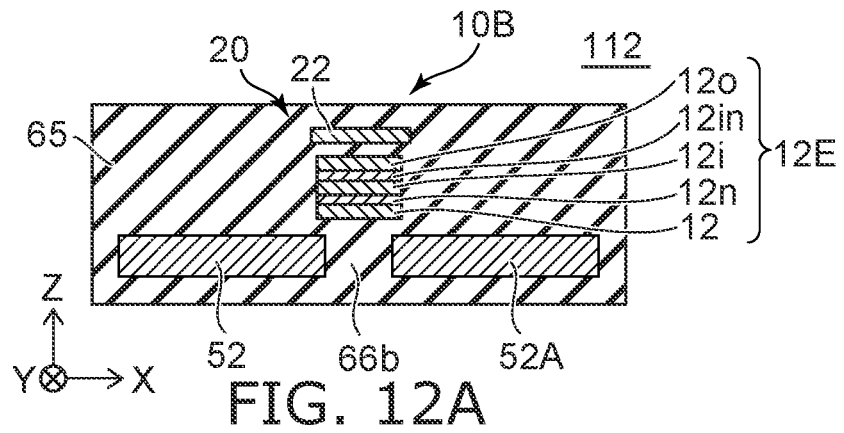
FIGS. 12A to 12C are schematic cross-sectional views illustrating the magnetic sensor according to the third embodiment.
Figure 12B:
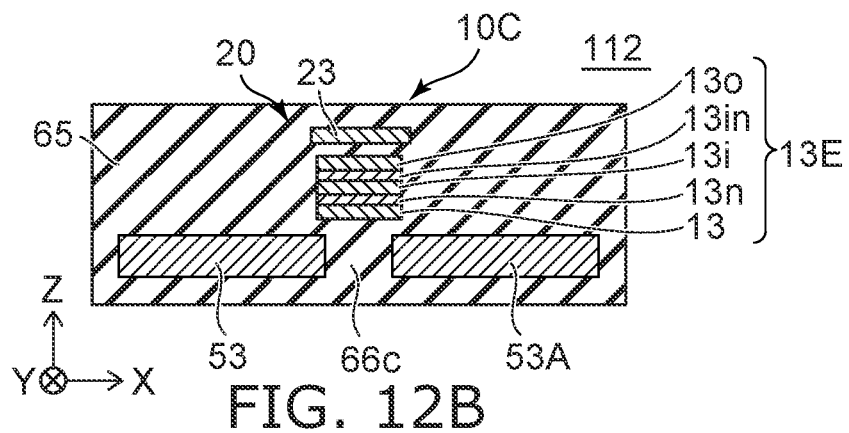
Figure 12C:
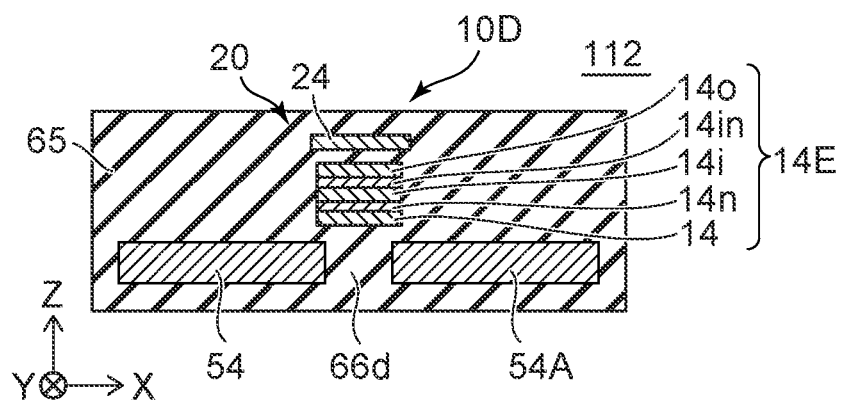

FIGS. 12A to 12C are schematic cross-sectional views illustrating the magnetic sensor according to the third embodiment.

Figure 13A:
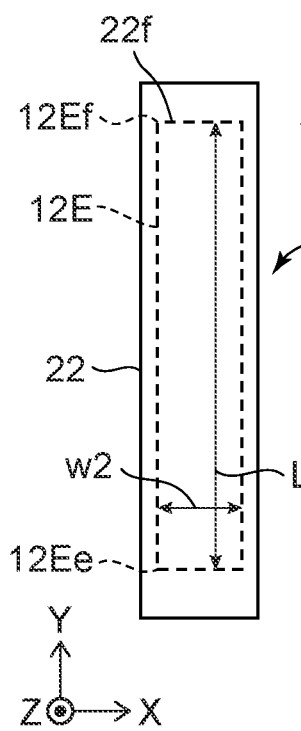
FIGS. 13A to 13C are schematic cross-sectional views illustrating the magnetic sensor according to the third embodiment.
Figure 13B:
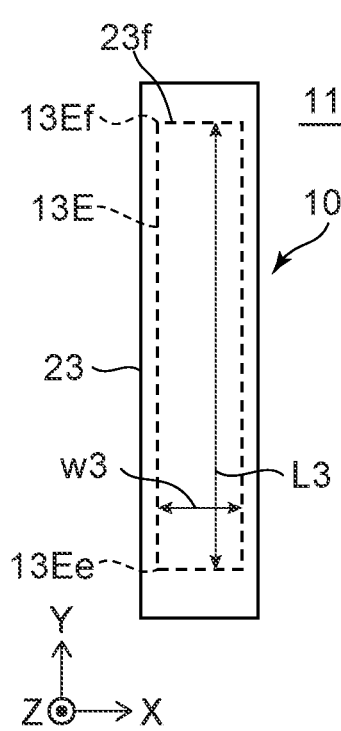
Figure 13C:
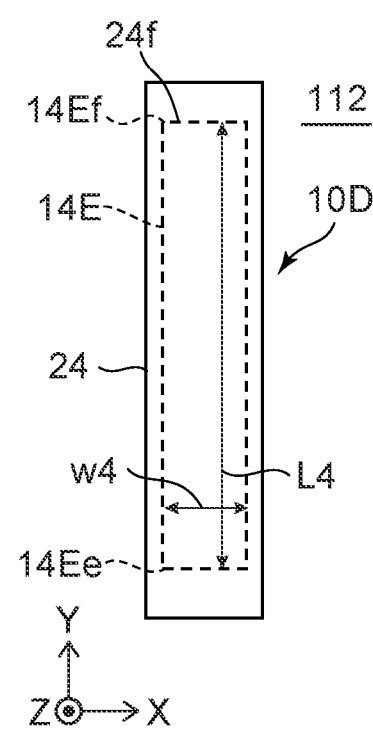

FIGS. 13A to 13C are schematic plan views illustrating the magnetic sensor according to the third embodiment.

As shown in FIG. 10, the magnetic sensor 112 according to the embodiment includes a second sensor part 10B, a third sensor part 10C, and a fourth sensor part 10D in addition to the first sensor part 10A. The second sensor part 10B includes a second magnetic element 12E. The third sensor part 10C includes a third magnetic element 13E. The fourth sensor part 10D includes a fourth magnetic element 14E.

The first magnetic element 11E includes the first end portion 11Ee and the first other-end portion 11Ef. The direction from the first end portion 11Ee toward the first other-end portion 11Ef is along the second direction (e.g., the Y-axis direction). The second magnetic element 12E includes a second end portion 12Ee and a second other-end portion 12Ef. The direction from the second end portion 12Ee toward the second other-end portion 12Ef is along the second direction. The third magnetic element 13E includes a third end portion 13Ee and a third other-end portion 13Ef. The direction from the third end portion 13Ee toward the third other-end portion 13Ef is along the second direction. The fourth magnetic element 14E includes a fourth end portion 14Ee and a fourth other-end portion 14Ef. The direction from the fourth end portion 14Ee toward the fourth other-end portion 14Ef is along the second direction.

For example, the first other-end portion 11Ef is electrically connected with the second end portion 12Ee. The first end portion 11Ee is electrically connected with the third end portion 13Ee. The third other-end portion 13Ef is electrically connected with the fourth end portion 14Ee. The second other-end portion 12Ef is electrically connected with the fourth other-end portion 14Ef. For example, the first to fourth magnetic elements 11E to 14E have a bridge connection.

The element current circuit 75 is configured to supply an element current to the first magnetic element 11E, the second magnetic element 12E, the third magnetic element 13E, and the fourth magnetic element 14E. In the example, the element current circuit 75 is configured to supply the element current Id between a first connection point CP1 and a second connection point CP2, in which the first connection point CP1 is between the first end portion 11Ee and the third end portion 13Ee, and the second connection point CP2 is between the second other-end portion 12Ef and the fourth other-end portion 14Ef.

As shown in FIG. 10, the magnetic sensor 112 may include a detection circuit 73. The detection circuit 73 may be included in the circuit part 70. The detection circuit 73 is configured to detect the change of the potential between a third connection point CP3 and a fourth connection point CP4, in which the third connection point CP3 is between the first other-end portion 11Ef and the second end portion 12Ee, and the fourth connection point CP4 is between the third other-end portion 13Ef and the fourth end portion 14Ee. By using a bridge circuit that includes multiple magnetic elements, the noise can be further suppressed. Detection with higher sensitivity is possible.

As shown in FIG. 11, the conductive member 20 includes a second corresponding portion 22, a third corresponding portion 23, and a fourth corresponding portion 24 in addition to the first corresponding portion 21. The second corresponding portion 22 is along the second magnetic element 12E. The third corresponding portion 23 is along the third magnetic element 13E. The fourth corresponding portion 24 is along the fourth magnetic element 14E.

For example, the second corresponding portion 22 overlaps the second magnetic element 12E in the Z-axis direction (referring to FIG. 12A). For example, the third corresponding portion 23 overlaps the third magnetic element 13E in the Z-axis direction (referring to FIG. 12B). For example, the fourth corresponding portion 24 overlaps the fourth magnetic element 14E in the Z-axis direction (referring to FIG. 12C).

As shown in FIG. 11, for example, the first corresponding portion 21 includes the first portion 21e that corresponds to the first end portion 11Ee, and the first other-portion 21f that corresponds to the first other-end portion 11Ef. For example, the first portion 21e overlaps the first end portion 11Ee in the Z-axis direction. The first other-portion 21f overlaps the first other-end portion 11Ef in the Z-axis direction.

As shown in FIG. 11, for example, the second corresponding portion 22 includes a second portion 22e that corresponds to the second end portion 12Ee, and a second other-portion 22f that corresponds to the second other-end portion 12Ef. For example, the second portion 22e overlaps the second end portion 12Ee in the Z-axis direction. The second other-portion 22f overlaps the second other-end portion 12Ef in the Z-axis direction.

As shown in FIG. 11, for example, the third corresponding portion 23 includes a third portion 23e that corresponds to the third end portion 13Ee, and a third other-portion 23f that corresponds to the third other-end portion 13Ef. For example, the third portion 23e overlaps the third end portion 13Ee in the Z-axis direction. The third other-portion 23f overlaps the third other-end portion 13Ef in the Z-axis direction.

As shown in FIG. 11, for example, the fourth corresponding portion 24 includes a fourth portion 24e that corresponds to the fourth end portion 14Ee, and a fourth other-portion 24f that corresponds to the fourth other-end portion 14Ef. For example, the fourth portion 24e overlaps the fourth end portion 14Ee in the Z-axis direction. The fourth other-portion 24f overlaps the fourth other-end portion 14Ef in the Z-axis direction.

The first current circuit 71 is configured to supply the first current I1 that includes the alternating current component to the first corresponding portion 21, the second corresponding portion 22, the third corresponding portion 23, and the fourth corresponding portion 24.

In the example, the first portion 21e is electrically connected with the third portion 23e. The first other-portion 21f is electrically connected with the second portion 22e. The third other-portion 23f is electrically connected with the fourth portion 24e. The second other-portion 22f is electrically connected with the fourth other-portion 24f. In the example, the first current circuit 71 is configured to supply the first current I1 that includes the alternating current component between a fifth connection point CP5 and a sixth connection point CP6, in which the fifth connection point CP5 is between the first other-portion 21f and the second portion 22e, and the sixth connection point CP6 is between the third other-portion 23f and the fourth portion 24e.

One time at which the first current I1 is supplied to the conductive member 20 is taken as a first time. At the first time, the element current Id flows through the first magnetic element 11E in the orientation from the first end portion 11Ee toward the first other-end portion 11Ef. At the first time, the element current Id flows through the second magnetic element 12E in the orientation from the second end portion 12Ee toward the second other-end portion 12Ef. At the first time, the element current Id flows through the third magnetic element 13E in the orientation from the third end portion 13Ee toward the third other-end portion 13Ef. At the first time, the element current Id flows through the fourth magnetic element 14E in the orientation from the fourth end portion 14Ee toward the fourth other-end portion 14Ef.

At the first time, the first current I1 flows through the first corresponding portion 21 in the orientation from the first other-portion 21f toward the first portion 21e. At the first time, the first current I1 flows through the second corresponding portion 22 in the orientation from the second portion 22e toward the second other-portion 22f. At the first time, the first current I1 flows through the third corresponding portion 23 in the orientation from the third portion 23e toward the third other-portion 23f. The first current I1 flows through the fourth corresponding portion 24 in the orientation from the fourth other-portion 24f toward the fourth portion 24e.

The magnetic field that is due to the first current I1 flowing through the first corresponding portion 21 is applied to the first magnetic element 11E. The magnetic field that is due to the first current I1 flowing through the second corresponding portion 22 is applied to the second magnetic element 12E. The magnetic field that is due to the first current I1 flowing through the third corresponding portion 23 is applied to the third magnetic element 13E. The magnetic field that is due to the first current I1 flowing through the fourth corresponding portion 24 is applied to the fourth magnetic element 14E.

For example, the relationship between the orientation of the element current Id flowing through the second magnetic element 12E at the first time and the orientation of the first current I1 flowing through the second corresponding portion 22 at the first time is opposite to (the opposite phase of) the relationship between the orientation of the first current I1 flowing through the first corresponding portion 21 at the first time and the orientation of the element current Id flowing through the first magnetic element 11E. The relationship between the orientation of the first current I1 flowing through the fourth corresponding portion 24 at the first time and the orientation of the element current Id flowing through the fourth magnetic element 14E is opposite to (the opposite phase of) the relationship between the orientation of the first current I1 flowing through the third corresponding portion 23 at the first time and the orientation of the element current Id flowing through the third magnetic element 13E.

The noise can be further suppressed by such a current flowing in the multiple magnetic elements that have the bridge connection.

As shown in FIG. 12A, the second magnetic element 12E includes a second magnetic layer 12, a second counter magnetic layer 12o, a second intermediate magnetic layer 12i, a second nonmagnetic layer 12n, and a second intermediate nonmagnetic layer 12in. The direction from the second magnetic layer 12 toward the second counter magnetic layer 12o is along the first direction (the Z-axis direction). The second intermediate magnetic layer 12i is located between the second magnetic layer 12 and the second counter magnetic layer 12o. The second nonmagnetic layer 12n is located between the second magnetic layer 12 and the second intermediate magnetic layer 12i. The second intermediate nonmagnetic layer 12in is located between the second intermediate magnetic layer 12i and the second counter magnetic layer 12o.

As shown in FIG. 12B, the third magnetic element 13E includes a third magnetic layer 13, a third counter magnetic layer 13o, a third intermediate magnetic layer 13i, a third nonmagnetic layer 13n, and a third intermediate nonmagnetic layer 13in. The direction from the third magnetic layer 13 toward the third counter magnetic layer 13o is along the first direction (the Z-axis direction). The third intermediate magnetic layer 13i is located between the third magnetic layer 13 and the third counter magnetic layer 13o. The third nonmagnetic layer 13n is located between the third magnetic layer 13 and the third intermediate magnetic layer 13i. The third intermediate nonmagnetic layer 13in is located between the third intermediate magnetic layer 13i and the third counter magnetic layer 13o.

As shown in FIG. 12C, the fourth magnetic element 14E includes a fourth magnetic layer 14, a fourth counter magnetic layer 14o, a fourth intermediate magnetic layer 14i, a fourth nonmagnetic layer 14n, and a fourth intermediate nonmagnetic layer 14in. The direction from the fourth magnetic layer 14 toward the fourth counter magnetic layer 14o is along the first direction (the Z-axis direction). The fourth intermediate magnetic layer 14i is located between the fourth magnetic layer 14 and the fourth counter magnetic layer 14o. The fourth nonmagnetic layer 14n is located between the fourth magnetic layer 14 and the fourth intermediate magnetic layer 14i. The fourth intermediate nonmagnetic layer 14in is located between the fourth intermediate magnetic layer 14i and the fourth counter magnetic layer 14o.

As shown in FIG. 12A, the second sensor part 10B may further include a second magnetic member 52 and a second counter magnetic member 52A. The direction from the second magnetic member 52 toward the second counter magnetic member 52A is along the third direction (e.g., the X-axis direction). The second magnetic element 12E overlaps a region 66b between the second magnetic member 52 and the second counter magnetic member 52A in the first direction (the Z-axis direction). The region 66b may be, for example, a portion of the insulating member 65. For example, a portion of the second magnetic element 12E overlaps a portion of the second magnetic member 52 in the first direction. Another portion of the second magnetic element 12E overlaps a portion of the second counter magnetic member 52A in the first direction.

As shown in FIG. 12B, the third sensor part 10C may further include a third magnetic member 53 and a third counter magnetic member 53A. The direction from the third magnetic member 53 toward the third counter magnetic member 53A is along the third direction (e.g., the X-axis direction). The third magnetic element 13E overlaps a region 66c between the third magnetic member 53 and the third counter magnetic member 53A in the first direction (the Z-axis direction). The region 66c may be, for example, a portion of the insulating member 65. For example, a portion of the third magnetic element 13E overlaps a portion of the third magnetic member 53 in the first direction. Another portion of the third magnetic element 13E overlaps a portion of the third counter magnetic member 53A in the first direction.

As shown in FIG. 12C, the fourth sensor part 10D may further include a fourth magnetic member 54 and a fourth counter magnetic member 54A. The direction from the fourth magnetic member 54 toward the fourth counter magnetic member 54A is along the third direction (e.g., the X-axis direction). The fourth magnetic element 14E overlaps a region 66d between the fourth magnetic member 54 and the fourth counter magnetic member 54A in the first direction (the Z-axis direction). The region 66d may be, for example, a portion of the insulating member 65. For example, a portion of the fourth magnetic element 14E overlaps a portion of the fourth magnetic member 54 in the first direction. Another portion of the fourth magnetic element 14E overlaps a portion of the fourth counter magnetic member 54A in the first direction.

As shown in FIG. 13A, the length along the second direction (the Y-axis direction) of the second magnetic element 12E is taken as a second length L2. The length along the third direction (e.g., the X-axis direction) of the second magnetic element 12E is taken as a second width w2. For example, the second length L2 is greater than the second width w2. For example, the magnetization of the magnetic layer included in the second magnetic element 12E is along the Y-axis direction.

As shown in FIG. 13B, the length along the second direction (the Y-axis direction) of the third magnetic element 13E is taken as a third length L3. The length along the third direction (e.g., the X-axis direction) of the third magnetic element 13E is taken as a third width w3. For example, the third length L3 is greater than the third width w3. For example, the magnetization of the magnetic layer included in the third magnetic element 13E is along the Y-axis direction.

As shown in FIG. 13C, the length along the second direction (the Y-axis direction) of the fourth magnetic element 14E is taken as a fourth length L4. The length along the third direction (e.g., the X-axis direction) of the fourth magnetic element 14E is taken as a fourth width w4. For example, the fourth length L4 is greater than the fourth width w4. For example, the magnetization of the magnetic layer included in the fourth magnetic element 14E is along the Y-axis direction.

The configurations (including the materials) of the second magnetic layer 12, the third magnetic layer 13, and the fourth magnetic layer 14 may be similar to the configuration (including the material) of the first magnetic layer 11. The configurations (including the materials) of the second counter magnetic layer 12o, the third counter magnetic layer 13o, and the fourth counter magnetic layer 14o may be similar to the configuration (including the material) of the first counter magnetic layer 11o. The configurations (including the materials) of the second intermediate magnetic layer 12i, the third intermediate magnetic layer 13i, and the fourth intermediate magnetic layer 14i may be similar to the configuration (including the material) of the first intermediate magnetic layer 11i. The configurations (including the materials) of the second nonmagnetic layer 12n, the third nonmagnetic layer 13n, and the fourth nonmagnetic layer 14n may be similar to the configuration (including the material) of the first nonmagnetic layer 11n. The configurations (including the materials) of the second intermediate nonmagnetic layer 12in, the third intermediate nonmagnetic layer 13in, and the fourth intermediate nonmagnetic layer 14in may be similar to the configuration (including the material) of the first intermediate nonmagnetic layer 11in.

At least one of the second sensor part 10B, the third sensor part 10C, or the fourth sensor part 10D may include magnetic parts similar to the first side magnetic part 11S and the first counter side magnetic part 11SA described with reference to the first sensor part 10A. At least one of the second sensor part 10B, the third sensor part 10C, or the fourth sensor part 10D may include stacked magnetic layers similar to the first stacked magnetic layer 11sL and the first counter stacked magnetic layer 11osL described with reference to the first sensor part 10A.

FIGS. 14A to 14C are schematic views illustrating magnetic sensors according to the third embodiment.

The configurations of magnetic sensors 112a to 112c illustrated in FIGS. 14A to 14C may be combined with the configuration of the magnetic sensor 112 illustrated in FIG. 10.

In the magnetic sensor 112a as shown in FIG. 14A, the first portion 21e is electrically connected with the second other-portion 22f. The first other-portion 21f is electrically connected with the fourth portion 24e. The third portion 23e is electrically connected with the fourth other-portion 24f. The third other-portion 23f is electrically connected with the second portion 22e.

In the magnetic sensor 112a, the first current circuit 71 is configured to supply the first current I1 between a seventh connection point CP7 and an eighth connection point CP8, in which the seventh connection point CP7 is between the first portion 21e and the second other-portion 22f, and the eighth connection point CP8 is between the third portion 23e and the fourth other-portion 24f.

At one time (the first time) in the magnetic sensor 112a, the first current I1 has the orientation from the first other-portion 21f toward the first portion 21e, the orientation from the second portion 22e toward the second other-portion 22f, the orientation from the third portion 23e toward the third other-portion 23f, and the orientation from the fourth other-portion 24f toward the fourth portion 24e.

In the magnetic sensor 112b as shown in FIG. 14B, the first other-portion 21f is electrically connected with the fourth portion 24e. The third other-portion 23f is electrically connected with the second portion 22e. The second other-portion 22f is electrically connected with the fourth other-portion 24f.

In the magnetic sensor 112b, the first current circuit 71 is configured to supply the first current I1 between the first portion 21e and the third portion 23e.

At one time (the first time) in the magnetic sensor 112b, the first current I1 has the orientation from the first other-portion 21f toward the first portion 21e, the orientation from the second portion 22e toward the second other-portion 22f, the orientation from the third portion 23e toward the third other-portion 23f, and the orientation from the fourth other-portion 24f toward the fourth portion 24e.

In the magnetic sensor 112c as shown in FIG. 14C, the first portion 21e is electrically connected with the second other-portion 22f, the third other-portion 23f, and the fourth portion 24e. The first other-portion 21f is electrically connected with the second portion 22e, the third portion 23e, and the fourth other-portion 24f.

In the magnetic sensor 112c, the first current circuit 71 is configured to supply the first current I1 that includes the alternating current between a ninth connection point CP9 and a tenth connection point CP10, in which the ninth connection point CP9 is between the first portion 21e, the second other-portion 22f, the third other-portion 23f, and the fourth portion 24e, and the tenth connection point CP10 is between the first other-portion 21f, the second portion 22e, the third portion 23e, and the fourth other-portion 24f.

At one time (the first time) in the magnetic sensor 112c, the first current I1 has the orientation from the first other-portion 21f toward the first portion 21e, the orientation from the second portion 22e toward the second other-portion 22f, the orientation from the third portion 23e toward the third other-portion 23f, and the orientation from the fourth other-portion 24f toward the fourth portion 24e.

In the magnetic sensors 112a to 112c as well, it is possible to suppress noise and detect with high sensitivity.

Figures 15A, 15B:
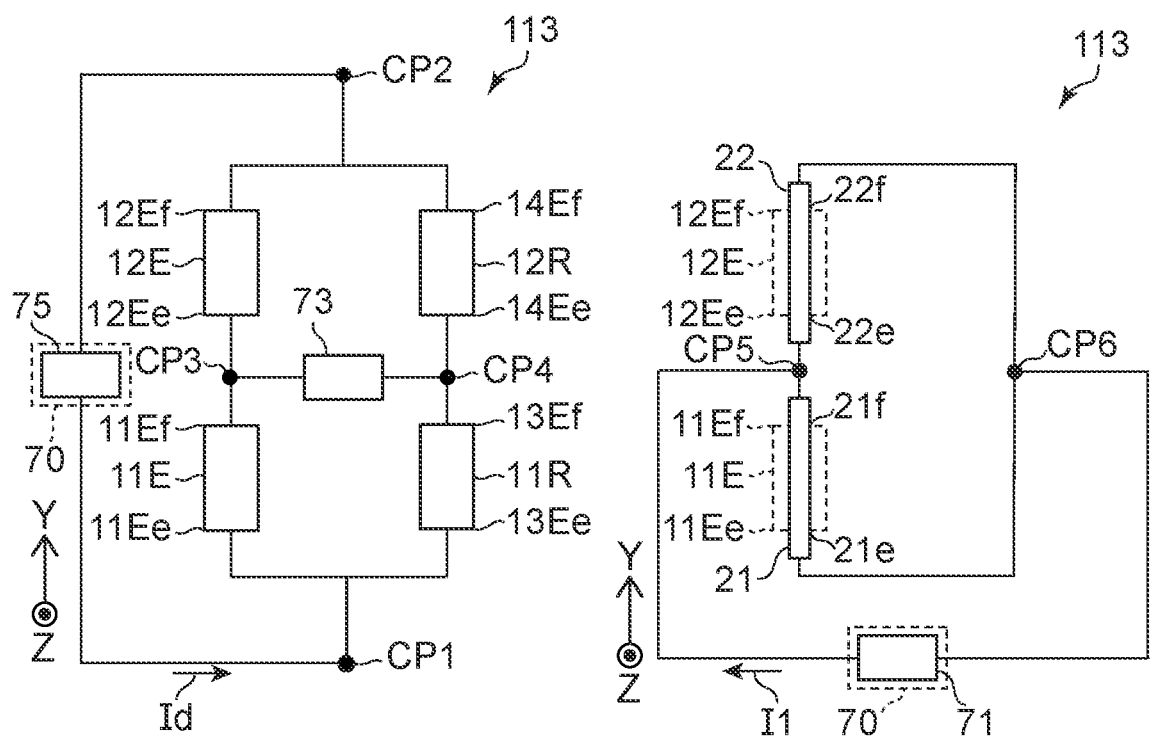
FIGS. 15A and 15B are schematic views illustrating a magnetic sensor according to the third embodiment.

FIGS. 15A and 15B are schematic views illustrating a magnetic sensor according to the third embodiment.

As shown in FIG. 15A, the magnetic sensor 113 according to the embodiment includes the first magnetic element 11E, the second magnetic element 12E, a first resistance element 11R, and a second resistance element 12R. Otherwise, the configuration of the magnetic sensor 113 may be, for example, the same as the magnetic sensor 110, etc.

The first magnetic element 11E includes the first end portion 11Ee and the first other-end portion 11Ef. The direction from the first end portion 11Ee toward the first other-end portion 11Ef is along the second direction (e.g., the Y-axis direction). The second magnetic element 12E includes the second end portion 12Ee and the second other-end portion 12Ef. The direction from the second end portion 12Ee toward the second other-end portion 12Ef is along the second direction. The first resistance element 11R includes the third end portion 13Ee and the third other-end portion 13Ef. The direction from the third end portion 13Ee toward the third other-end portion 13Ef is along the second direction. The second resistance element 12R includes the fourth end portion 14Ee and the fourth other-end portion 14Ef. The direction from the fourth end portion 14Ee toward the fourth other-end portion 14Ef is along the second direction.

The conductive member 20 includes the first corresponding portion 21 and the second corresponding portion 22. The first corresponding portion 21 is along the first magnetic element 11E. The second corresponding portion 22 is along the second magnetic element 12E.

The first corresponding portion 21 includes the first portion 21e that corresponds to the first end portion 11Ee, and the first other-portion 21f that corresponds to the first other-end portion 11Ef. The second corresponding portion 22 includes the second portion 22e that corresponds to the second end portion 12Ee, and the second other-portion 22f that corresponds to the second other-end portion 12Ef.

In the magnetic sensor 113, the first end portion 11Ee of the first magnetic element 11E is electrically connected with the third end portion 13Ee of the first resistance element 11R. The first other-end portion 11Ef of the first magnetic element 11E is electrically connected with the second end portion 12Ee of the second magnetic element 12E. The third other-end portion 13Ef of the first resistance element 11R is electrically connected with the fourth end portion 14Ee of the second resistance element 12R. The second other-end portion 12Ef of the second magnetic element 12E is electrically connected with the fourth other-end portion 14Ef of the second resistance element 12R.

The element current circuit 75 is configured to supply the element current Id between the first connection point CP1 and the second connection point CP2, in which the first connection point CP1 is between the first end portion 11Ee and the third end portion 13Ee, and the second connection point CP2 is between the second other-end portion 12Ef and the fourth other-end portion 14Ef.

The detection circuit 73 is configured to detect the change of the potential between the third connection point CP3 and the fourth connection point CP4, in which the third connection point CP3 is between the first other-end portion 11Ef and the second end portion 12Ee, and the fourth connection point CP4 is between the third other-end portion 13Ef and the fourth end portion 14Ee.

As shown in FIG. 15B, the first other-portion 21f is electrically connected with the second portion 22e. The first portion 21e is electrically connected with the second other-portion 22f. The first current circuit 71 is configured to supply the first current I1 between the fifth connection point CP5 and the sixth connection point CP6, in which the fifth connection point CP5 is between the first other-portion 21f and the second portion 22e, and the sixth connection point CP6 is between the first portion 21e and the second other-portion 22f. In the magnetic sensor 113 as well, it is possible to suppress noise and detect with high sensitivity.

Figures 16A, 16B:
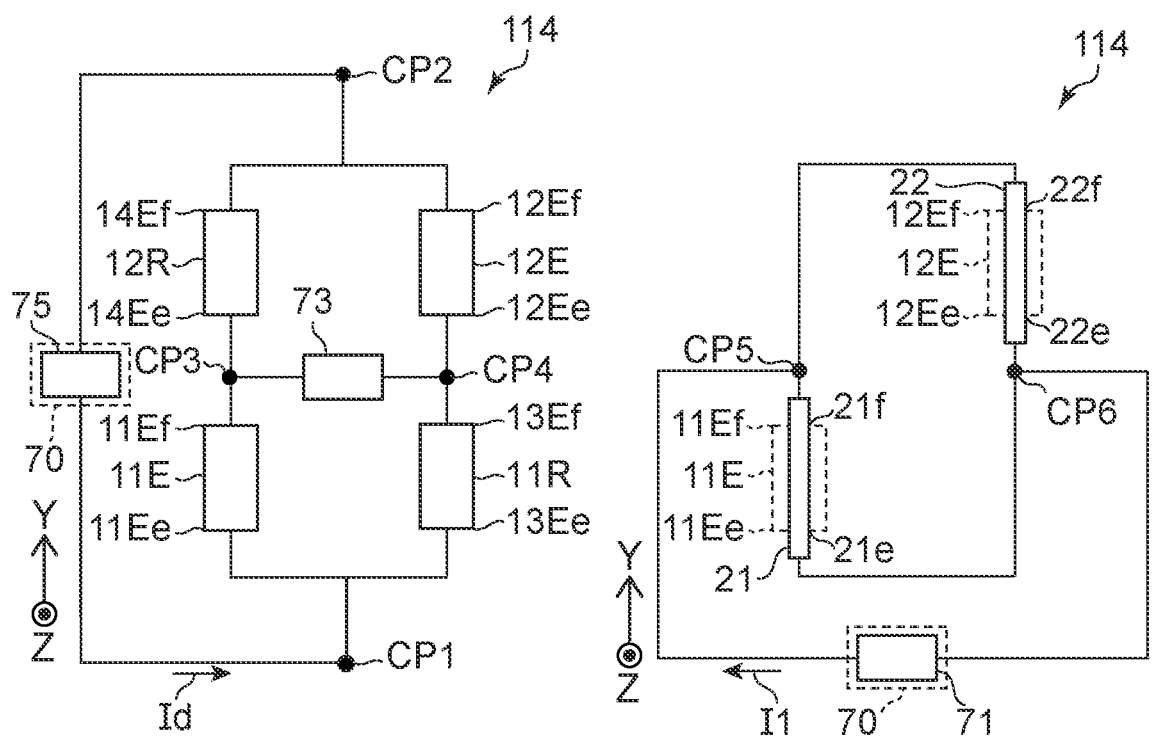
FIGS. 16A and 16B are schematic views illustrating a magnetic sensor according to the third embodiment.

FIGS. 16A and 16B are schematic views illustrating a magnetic sensor according to the third embodiment.

As shown in FIG. 16A, the magnetic sensor 114 according to the embodiment includes the first magnetic element 11E, the second magnetic element 12E, the first resistance element 11R, and the second resistance element 12R. Otherwise, the configuration of the magnetic sensor 114 may be, for example, the same as the magnetic sensor 110, etc.

In the magnetic sensor 114 as shown in FIG. 16A, the first end portion 11Ee of the first magnetic element 11E is electrically connected with the third end portion 13Ee of the first resistance element 11R. The first other-end portion 11Ef of the first magnetic element 11E is electrically connected with the fourth end portion 14Ee of the second resistance element 12R. The third other-end portion 13Ef of the first resistance element 11R is electrically connected with the second end portion 12Ee of the second magnetic element 12E. The fourth other-end portion 14Ef of the second resistance element 12R is electrically connected with the second other-end portion 12Ef of the second magnetic element 12E.

The element current circuit 75 is configured to supply the element current Id between the first connection point CP1 and the second connection point CP2, in which the first connection point CP1 is between the first end portion 11Ee and the third end portion 13Ee, and the second connection point CP2 is between the fourth other-end portion 14Ef and the second other-end portion 12Ef.

The magnetic sensor 114 may include the detection circuit 73. The detection circuit 73 is configured to detect the change of the potential between the third connection point CP3 and the fourth connection point CP4, in which the third connection point CP3 is between the first other-end portion 11Ef and the fourth end portion 14Ee, and the fourth connection point CP4 is between the third other-end portion 13Ef and the second end portion 12Ee.

As shown in FIG. 16B, the first portion 21e of the first corresponding portion 21 is electrically connected with the second portion 22e of the second corresponding portion 22. The first other-portion 21f of the first corresponding portion 21 is electrically connected with the second other-portion 22f of the second corresponding portion 22.

The first current circuit 71 is configured to supply the first current I1 between the fifth connection point CP5 and the sixth connection point CP6, in which the fifth connection point CP5 is between the first other-portion 21f and the second other-portion 22f, and the sixth connection point CP6 is between the first portion 21e and the second portion 22e.

Fourth Embodiment

A fourth embodiment relates to an inspection device. As described below, the inspection device may include a diagnostic device.

Figure 17:
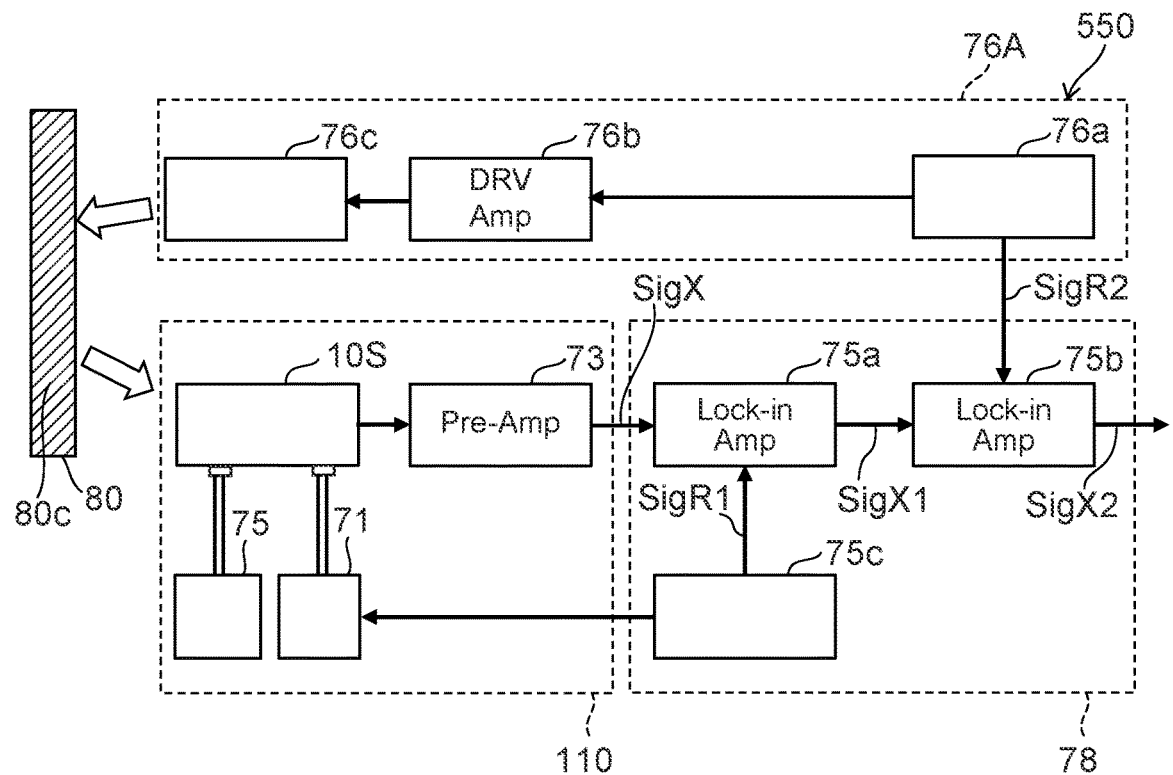
FIG. 17 is a schematic view illustrating an inspection device according to a fourth embodiment.

FIG. 17 is a schematic view illustrating an inspection device according to the fourth embodiment.

As shown in FIG. 17, the inspection device 550 according to the embodiment includes a processor 78 and the magnetic sensor (in the example of FIG. 17, the magnetic sensor 110) according to the embodiment. The processor 78 processes an output signal SigX obtained from the magnetic sensor 110. In the example, the processor 78 includes a sensor control circuit part 75c, a first lock-in amplifier 75a, and a second lock-in amplifier 75b. For example, the first current circuit 71 is controlled by the sensor control circuit part 75c; and the first current I1 that includes the alternating current component is supplied from the first current circuit 71 to a sensor part 10S. The frequency of the alternating current component of the first current I1 is, for example, not more than 100 kHz. The element current Id is supplied from the element current circuit 75 to the sensor part 10S. The sensor part 10S includes, for example, at least one magnetic element. The change of the potential of the sensor part 10S is detected by the detection circuit 73. For example, the output of the detection circuit 73 is the output signal SigX.

In the example, the inspection device 550 includes a magnetic field application part 76A. The magnetic field application part 76A is configured to apply a magnetic field to a detection object 80. The detection object 80 is, for example, the inspection object. The detection object 80 includes at least an inspection conductive member 80c such as a metal, etc. For example, an eddy current is generated in the inspection conductive member 80c when the magnetic field due to the magnetic field application part 76A is applied to the inspection conductive member 80c. The state of the eddy current changes when there is a flaw or the like in the inspection conductive member 80c. The state (e.g., the flaw, etc.) of the inspection conductive member 80c can be inspected by the magnetic sensor (e.g., the magnetic sensor 110, etc.) detecting the magnetic field due to the eddy current. The magnetic field application part 76A is, for example, an eddy current generator.

In the example, the magnetic field application part 76A includes an application control circuit part 76a, a drive amplifier 76b, and a coil 76c. A current is supplied to the drive amplifier 76b by the control by the application control circuit part 76a. The current is, for example, an alternating current. The frequency of the current is, for example, an eddy current excitation frequency. The eddy current excitation frequency is, for example, not less than 10 Hz and not more than 100 kHz. The eddy current excitation frequency may be, for example, less than 100 kHz.

For example, information (which may be, for example, a signal) that relates to the frequency of the alternating current component of the first current I1 is supplied from the sensor control circuit part 75c to the first lock-in amplifier 75a as a reference wave (a reference signal). The output of the first lock-in amplifier 75a is supplied to the second lock-in amplifier 75b. Information (which may be, for example, a signal) that relates to the eddy current excitation frequency is supplied from the application control circuit part 76a to the second lock-in amplifier 75b as a reference wave (a reference signal). The second lock-in amplifier 75b is configured to output a signal component corresponding to the eddy current excitation frequency.

Thus, for example, the processor 78 includes the first lock-in amplifier 75a. The output signal SigX that is obtained from the magnetic sensor 110 and a signal SigR1 that corresponds to the frequency of the alternating current component included in the first current I1 are input to the first lock-in amplifier 75a. The first lock-in amplifier 75a is configured to output an output signal SigX1 that uses the signal SigR1 corresponding to the frequency of the alternating current component included in the first current I1 as a reference wave (a reference signal). By providing the first lock-in amplifier 75a, it is possible to suppress noise and detect with high sensitivity.

The processor 78 may further include the second lock-in amplifier 75b. The output signal SigX1 of the first lock-in amplifier 75a and a signal SigR2 that corresponds to the frequency (the eddy current excitation frequency) of the supply signal (in the example, the magnetic field due to the magnetic field application part 76A) supplied toward the detection object 80 (the inspection object) are input to the second lock-in amplifier 75b. The second lock-in amplifier 75b is configured to output an output signal SigX2 that uses the signal SigR2 corresponding to the frequency of the supply signal supplied toward the detection object 80 (the inspection object) as a reference wave (a reference signal). By providing the second lock-in amplifier 75$b$, it is possible to further suppress noise and detect with even higher sensitivity.

An abnormality such as a flaw or the like of the inspection conductive member 80$c$ of the detection object 80 can be inspected by the inspection device 550.

Figure 18:
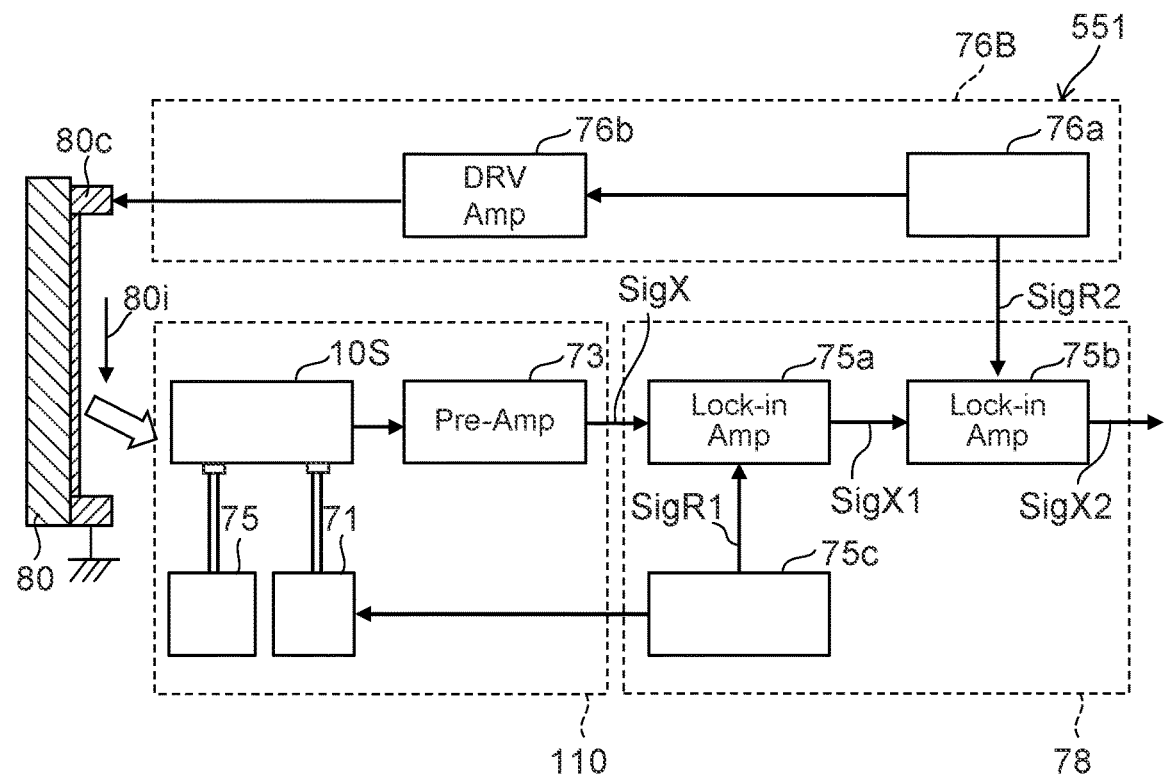
FIG. 18 is a schematic view illustrating an inspection device according to the fourth embodiment.

FIG. 18 is a schematic view illustrating an inspection device according to the fourth embodiment.

As shown in FIG. 18, the inspection device 551 according to the embodiment includes the processor 78 and the magnetic sensor (e.g., the magnetic sensor 110) according to the embodiment. The configurations of the magnetic sensor and the processor 78 of the inspection device 551 may be similar to those of the inspection device 550. In the example, the inspection device 551 includes a detection object driver 76B. The detection object driver 76B is configured to supply a current to the inspection conductive member 80$c$ included in the detection object 80. The inspection conductive member 80$c$ is, for example, wiring included in the detection object 80. A magnetic field that is due to a current 80$i$ flowing in the inspection conductive member 80$c$ is detected by the magnetic sensor 110. The inspection conductive member 80$c$ can be inspected based on an abnormality due to the detection result of the magnetic sensor 110. The detection object 80 may be, for example, an electronic device such as a semiconductor device, etc. The detection object 80 may be, for example, a battery, etc.

In the example, the detection object driver 76B includes the application control circuit part 76$a$ and the drive amplifier 76$b$. The drive amplifier 76$b$ is controlled by the application control circuit part 76$a$; and a current is supplied from the drive amplifier 76$b$ to the inspection conductive member 80$c$. The current is, for example, an alternating current. For example, the alternating current is supplied to the inspection conductive member 80$c$. The frequency of the alternating current is, for example, not less than 10 Hz and not more than 100 kHz. The frequency may be, for example, less than 100 kHz. In the example as well, for example, by providing the first lock-in amplifier 75$a$ and the second lock-in amplifier 75$b$, it is possible to suppress noise and detect with high sensitivity. In one example of the inspection device 551, multiple magnetic sensors (e.g., the multiple magnetic sensors 110) may be provided. The multiple magnetic sensors are, for example, a sensor array. The inspection conductive member 80$c$ can be inspected in a short period of time by the sensor array. In one example of the inspection device 551, the inspection conductive member 80$c$ may be inspected by scanning the magnetic sensor (e.g., the magnetic sensor 110).

Figure 19:
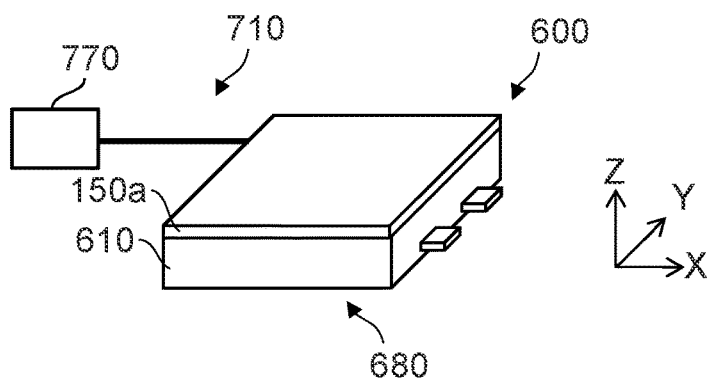
FIG. 19 is a schematic perspective view showing an inspection device according to the fourth embodiment.

FIG. 19 is a schematic perspective view showing an inspection device according to the fourth embodiment.

As shown in FIG. 19, the inspection device 710 according to the embodiment includes a magnetic sensor 150$a$ and a processor 770. The magnetic sensor 150$a$ may be the magnetic sensor according to one of the first to third embodiments or a modification of the magnetic sensor. The processor 770 processes an output signal obtained from the magnetic sensor 150$a$. The processor 770 may perform a comparison between a reference value and the signal obtained from the magnetic sensor 150$a$, etc. The processor 770 is configured to output an inspection result based on the processing result.

For example, an inspection object 680 is inspected by the inspection device 710. The inspection object 680 is, for example, an electronic device (including a semiconductor circuit, etc.). The inspection object 680 may be, for example, a battery 610, etc.

For example, the magnetic sensor 150$a$ according to the embodiment may be used together with the battery 610. For example, a battery system 600 includes the battery 610 and the magnetic sensor 150$a$. The magnetic sensor 150$a$ can detect a magnetic field generated by a current flowing in the battery 610.

Figure 20:
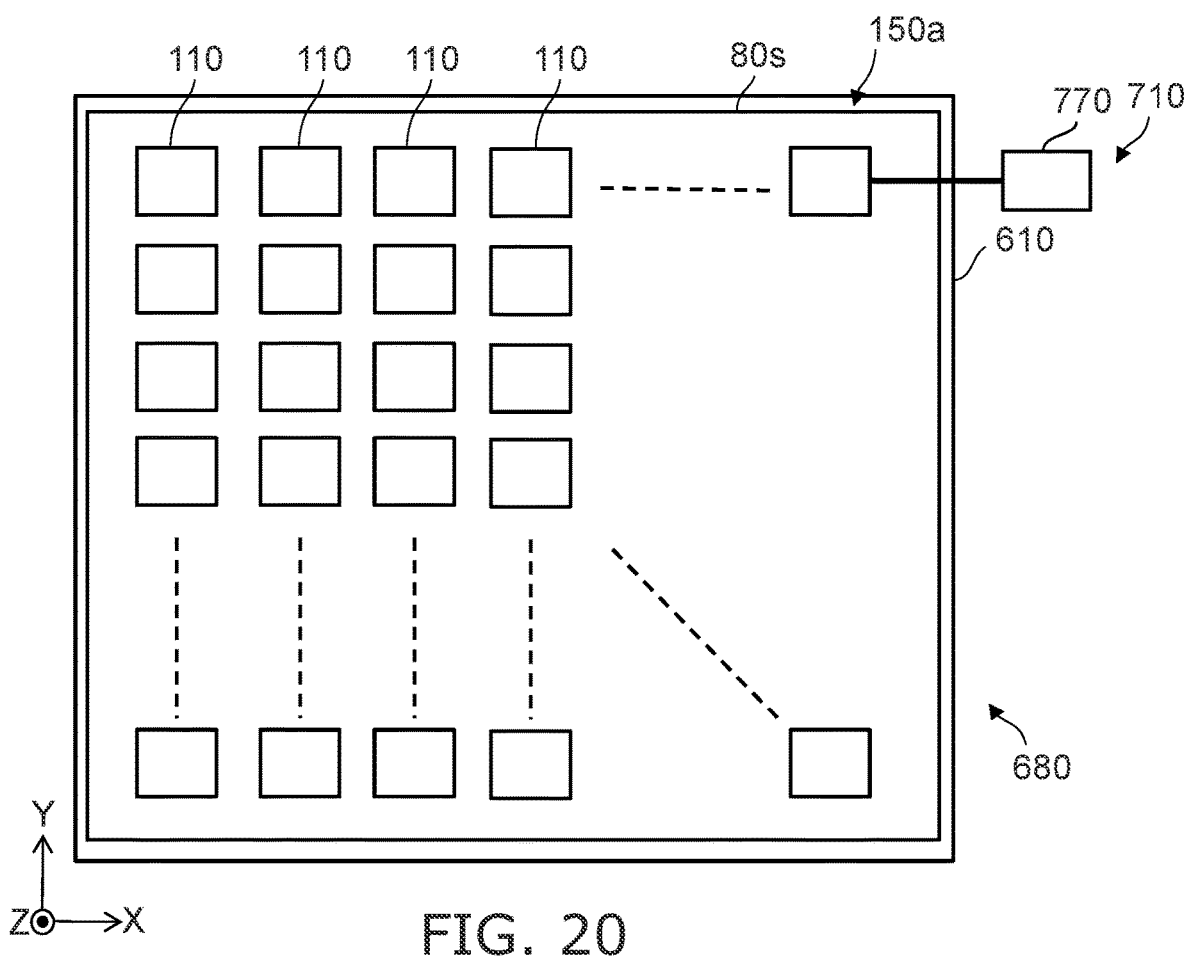
FIG. 20 is a schematic plan view showing the inspection device according to the fourth embodiment.

FIG. 20 is a schematic plan view showing the inspection device according to the fourth embodiment.

As shown in FIG. 20, the magnetic sensor 150$a$ includes, for example, multiple magnetic sensors according to the embodiment. In the example, the magnetic sensor 150$a$ includes multiple magnetic sensors (e.g., the magnetic sensor 110, etc.). For example, the multiple magnetic sensors are arranged along two directions (e.g., the X-axis direction and the Y-axis direction). For example, the multiple magnetic sensors 110 are located on a base body.

The magnetic sensor 150$a$ can detect a magnetic field generated by a current flowing in the inspection object 680 (which may be, for example, the battery 610). For example, an abnormal current flows in the battery 610 when the battery 610 approaches an abnormal state. The change of the state of the battery 610 can be known by the magnetic sensor 150$a$ detecting the abnormal current. For example, the entire battery 610 can be inspected in a short period of time by moving the sensor array in two directions while the magnetic sensor 150$a$ is proximate to the battery 610. The magnetic sensor 150$a$ may be used to inspect the battery 610 in the manufacturing process of the battery 610.

For example, the magnetic sensor according to the embodiment is applicable to the inspection device 710 such as a diagnostic device, etc. FIG. 21 is a schematic view showing the magnetic sensor and the inspection device according to the fourth embodiment.

As shown in FIG. 21, the diagnostic device 500 is an example of the inspection device 710 and includes the magnetic sensor 150. The magnetic sensor 150 includes the magnetic sensors described in reference to the first to third embodiments and modifications of the magnetic sensors.

In the diagnostic device 500, the magnetic sensor 150 is, for example, a magnetoencephalography device. The magnetoencephalography device detects a magnetic field generated by cranial nerves. When the magnetic sensor 150 is used in a magnetoencephalography device, the size of the magnetic element included in the magnetic sensor 150 is, for example, not less than 1 mm but less than 10 mm. The size is, for example, the length including the MFC.

As shown in FIG. 21, the magnetic sensor 150 (the magnetoencephalography device) is mounted to, for example, the head of a human body. The magnetic sensor 150 (the magnetoencephalography device) includes a sensor part 301. The magnetic sensor 150 (the magnetoencephalography device) may include multiple sensor parts 301. The number of the multiple sensor parts 301 is, for example, about 100 (e.g., not less than 50 and not more than 150). The multiple sensor parts 301 is provided on a flexible base body 302.

The magnetic sensor 150 may include, for example, a circuit for differential detection, etc. The magnetic sensor 150 may include a sensor other than a magnetic sensor (e.g., a potential terminal, an acceleration sensor, etc.).

The size of the magnetic sensor 150 is small compared to the size of a conventional SQUID magnetic sensor. Therefore, the mounting of the multiple sensor parts 301 is easy. The mounting of the multiple sensor parts 301 and the other circuits is easy. The multiple sensor parts 301 and the other sensors can be easily mounted together.

The base body 302 may include, for example, an elastic body such as a silicone resin, etc. For example, the multiple sensor parts 301 are linked to each other and provided in the base body 302. For example, the base body 302 can be closely adhered to the head.

An input/output cord 303 of the sensor part 301 is connected with a sensor driver 506 and a signal input/output part 504 of the diagnostic device 500. A magnetic field measurement is performed in the sensor part 301 based on electrical power from the sensor driver 506 and a control signal from the signal input/output part 504. The result is input to the signal input/output part 504. The signal that is obtained by the signal input/output part 504 is supplied to a signal processor 508. Processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography. For example, signal analysis to match the signal phases is performed in the signal analyzer 510.

The output of the signal analyzer 510 (the data for which the signal analysis is finished) is supplied to a data processor 512. Data analysis is performed in the data processor 512. It is possible to include image data such as, for example, MRI (Magnetic Resonance Imaging), etc., in the data analysis. It is possible to include, for example, scalp potential information such as EEG (Electroencephalogram), etc., in the data analysis. For example, a data part 514 of the MRI, the EEG, etc., is connected with the data processor 512. For example, nerve firing point analysis, inverse analysis, or the like is performed by the data analysis.

For example, the result of the data analysis is supplied to an imaging diagnostic part 516. Imaging is performed by the imaging diagnostic part 516. The diagnosis is supported by the imaging.

For example, the series of operations described above is controlled by a control mechanism 502. For example, necessary data such as preliminary signal data, metadata partway through the data processing, or the like is stored in a data server. The data server and the control mechanism may be integrated.

The diagnostic device 500 according to the embodiment includes the magnetic sensor 150, and a processor that processes the output signal obtained from the magnetic sensor 150. The processor includes, for example, at least one of the signal processor 508 or the data processor 512. The processor includes, for example, a computer, etc.

In the magnetic sensor 150 shown in FIG. 21, the sensor part 301 is mounted to the head of a human body. The sensor part 301 may be mounted to the chest of the human body. Magnetocardiography is possible thereby. For example, the sensor part 301 may be mounted to the abdomen of a pregnant woman. Palmoscopy of the fetus can be performed thereby.

It is favorable for the magnetic sensor device including the participant to be mounted inside a shielded room. For example, the effects of geomagnetism or magnetic noise can be suppressed thereby.

For example, a mechanism may be provided to locally shield the sensor part 301 or the measurement section of the human body. For example, a shield mechanism may be provided in the sensor part 301. For example, the signal analysis or the data processing may be effectively shielded.

According to the embodiment, the base body 302 may be flexible or may be substantially not flexible. In the example shown in FIG. 21, the base body 302 is a continuous membrane that is patterned into a hat-like configuration. The base body 302 may have a net configuration. For example, a good fit is obtained thereby. For example, the adhesion of the base body 302 to the human body is improved. The base body 302 may have a hard helmet-like configuration.

Figure 22:
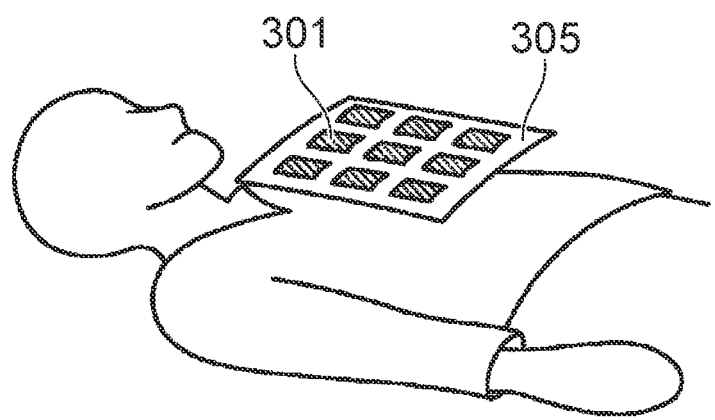
FIG. 22 is a schematic view showing the inspection device according to the fourth embodiment.

FIG. 22 is a schematic view showing the inspection device according to the fourth embodiment.

FIG. 22 is an example of a magnetocardiography device. In the example shown in FIG. 22, the sensor part 301 is provided on a hard base body 305 having a flat plate shape.

The input and output of the signal obtained from the sensor part 301 in the example shown in FIG. 22 are similar to the input and output described with reference to FIG. 21. The processing of the signal obtained from the sensor part 301 in the example shown in FIG. 22 is similar to the processing described with reference to FIG. 21.

There is a reference example in which a SQUID (Superconducting Quantum Interference Device) magnetic sensor is used as a device to measure a faint magnetic field such as a magnetic field emitted from a living body, etc. Because superconductivity is used in the reference example, the device is large; and the power consumption is large. The load on the measurement object (the patient) is large.

According to the embodiment, the device can be small. The power consumption can be suppressed. The load on the measurement object (the patient) can be reduced. According to the embodiment, the SN ratio of the magnetic field detection can be improved. The sensitivity can be increased.

Embodiments may include the following configurations (e.g., technological proposals).

Configuration 1

A magnetic sensor, comprising:
a first sensor part including
a first magnetic element,
a first side magnetic part, and
a first counter side magnetic part; and
a conductive member,
the conductive member including a first corresponding portion along the first magnetic element,
the first magnetic element including:
a first magnetic layer,
a first counter magnetic layer, a direction from the first magnetic layer toward the first counter magnetic layer being along a first direction, and
a first intermediate magnetic layer located between the first magnetic layer and the first counter magnetic layer,
the first side magnetic part including a first side magnetic layer,
the first counter side magnetic part including a first counter side magnetic layer,
the first intermediate magnetic layer being between the first side magnetic layer and the first counter side magnetic layer in a second direction crossing the first direction.

Configuration 2

The magnetic sensor according to Configuration 1, wherein
a distance along the second direction between the first side magnetic part and the first magnetic element is not more than 0.01 times a first length along the second direction of the first magnetic element.

Configuration 3

The magnetic sensor according to Configuration 1 or 2, wherein
the first magnetic element further includes:
a first nonmagnetic layer located between the first magnetic layer and the first intermediate magnetic layer; and a first intermediate nonmagnetic layer located between the first intermediate magnetic layer and the first counter magnetic layer, the first side magnetic part further includes a first stacked side magnetic layer, the first counter side magnetic part further includes a first counter stacked side magnetic layer, and the first counter magnetic layer is between the first stacked side magnetic layer and the first counter stacked side magnetic layer in the second direction.

Configuration 4

The magnetic sensor according to Configuration 3, wherein the first side magnetic part further includes a first side nonmagnetic layer located between the first side magnetic layer and the first stacked side magnetic layer, the first counter side magnetic part further includes a first counter side nonmagnetic layer located between the first counter side magnetic layer and the first counter stacked side magnetic layer, and the first side nonmagnetic layer and the first counter side nonmagnetic layer include a material included in the first intermediate nonmagnetic layer.

Configuration 5

A magnetic sensor, comprising:
a first sensor part including
a first magnetic element,
a first stacked magnetic layer, and
a first counter stacked magnetic layer; and
a conductive member, the conductive member including a first corresponding portion along the first magnetic element, the first magnetic element including
a first magnetic layer,
a first counter magnetic layer, a direction from the first magnetic layer toward the first counter magnetic layer being along a first direction,
a first intermediate magnetic layer located between the first magnetic layer and the first counter magnetic layer,
a first nonmagnetic layer located between the first magnetic layer and the first intermediate magnetic layer, and
a first intermediate nonmagnetic layer located between the first intermediate magnetic layer and the first counter magnetic layer, a direction from the first stacked magnetic layer toward the first counter stacked magnetic layer being along a second direction crossing the first direction, a portion of the first counter magnetic layer being between the first magnetic layer and the first stacked magnetic layer, an other portion of the first counter magnetic layer being between the first magnetic layer and the first counter stacked magnetic layer.

Configuration 6

The magnetic sensor according to Configuration 5, wherein the first stacked magnetic layer contacts the portion of the first counter magnetic layer, or a distance along the first direction between the first stacked magnetic layer and the portion of the first counter magnetic layer is not more than 0.001 times a thickness of the first counter magnetic layer, and the first counter stacked magnetic layer contacts the other portion of the first counter magnetic layer, or a distance along the first direction between the first counter stacked magnetic layer and the other portion of the first counter magnetic layer is not more than 0.001 times the thickness of the first counter magnetic layer.

Configuration 7

The magnetic sensor according to Configuration 5 or 6, wherein a length along the second direction of the first stacked magnetic layer is not less than 0.01 times and not more than 0.1 times a length along the second direction of the first magnetic element, and a length along the second direction of the first counter stacked magnetic layer is not less than 0.01 times and not more than 0.1 times the length along the second direction of the first magnetic element.

Configuration 8

The magnetic sensor according to any one of Configurations 1 to 7, wherein a first length along the second direction of the first magnetic element is greater than a first width of the first magnetic element along a direction crossing a plane including the first and second directions.

Configuration 9

The magnetic sensor according to any one of Configurations 1 to 8, wherein the first sensor part further includes a first magnetic member and a first counter magnetic member, a direction from the first magnetic member toward the first counter magnetic member is along a third direction crossing a plane including the first and second directions, and the first magnetic element overlaps a region between the first magnetic member and the first counter magnetic member in the first direction.

Configuration 10

The magnetic sensor according to Configuration 9, wherein a portion of the first magnetic element overlaps a portion of the first magnetic member in the first direction, and an other portion of the first magnetic element overlaps a portion of the first counter magnetic member in the first direction.

Configuration 11

The magnetic sensor according to any one of Configurations 1 to 10, wherein the first corresponding portion overlaps the first magnetic element in a direction crossing the second direction.

Configuration 12

The magnetic sensor according to Configuration 11, wherein the first magnetic element includes a first end portion and a first other-end portion, a direction from the first end portion toward the first other-end portion is along the second direction, the first corresponding portion includes a first portion and a first other-portion, the first portion corresponds to the first end portion, and the first other-portion corresponds to the first other-end portion.

Configuration 13

The magnetic sensor according to Configuration 12, wherein the first portion overlaps the first end portion in the first direction, and the first other-portion overlaps the first other-end portion in the first direction.

Configuration 14

The magnetic sensor according to any one of Configurations 11 to 13, wherein an electrical resistance of the first magnetic element has an even-function characteristic with respect to a current flowing in the first corresponding portion.

Configuration 15

The magnetic sensor according to any one of Configurations 1 to 7, wherein
an electrical resistance of the first magnetic element has an even-function characteristic with respect to a magnetic field applied to the first magnetic element.

Configuration 16

The magnetic sensor according to Configuration 11, further comprising:
a second sensor part including a second magnetic element;
a third sensor part including a third magnetic element;
a fourth sensor part including a fourth magnetic element;
an element current circuit; and
a first current circuit,
the first magnetic element including a first end portion and a first other-end portion,
a direction from the first end portion toward the first other-end portion being along the second direction,
the second magnetic element including a second end portion and a second other-end portion,
a direction from the second end portion toward the second other-end portion being along the second direction,
the third magnetic element including a third end portion and a third other-end portion,
a direction from the third end portion toward the third other-end portion being along the second direction,
the fourth magnetic element including a fourth end portion and a fourth other-end portion,
a direction from the fourth end portion toward the fourth other-end portion being along the second direction,
the conductive member including
a second corresponding portion along the second magnetic element,
a third corresponding portion along the third magnetic element, and
a fourth corresponding portion along the fourth magnetic element,
the first corresponding portion including a first portion and a first other-portion,
the first portion corresponding to the first end portion,
the first other-portion corresponding to the first other-end portion,
the second corresponding portion including a second portion and a second other-portion,
the second portion corresponding to the second end portion,
the second other-portion corresponding to the second other-end portion,
the third corresponding portion including a third portion and a third other-portion,
the third portion corresponding to the third end portion,
the third other-portion corresponding to the third other-end portion,
the fourth corresponding portion including a fourth portion and a fourth other-portion,
the fourth portion corresponding to the fourth end portion,
the fourth other-portion corresponding to the fourth other-end portion,
the element current circuit being configured to supply an element current to the first, second, third, and fourth magnetic elements,
the first current circuit being configured to supply a first current to the first, second, third, and fourth corresponding portions,
the first current including an alternating current component.

Configuration 17

The magnetic sensor according to Configuration 16, wherein
at a first time at which the first current is supplied to the conductive member:
the element current flows through the first magnetic element in an orientation from the first end portion toward the first other-end portion;
the element current flows through the second magnetic element in an orientation from the second end portion toward the second other-end portion;
the element current flows through the third magnetic element in an orientation from the third end portion toward the third other-end portion;
the element current flows through the fourth magnetic element in an orientation from the fourth end portion toward the fourth other-end portion;
the first current flows through the first corresponding portion in an orientation from the first other-portion toward the first portion;
the first current flows through the second corresponding portion in an orientation from the second portion toward the second other-portion;
the first current flows through the third corresponding portion in an orientation from the third portion toward the third other-portion; and
the first current flows through the fourth corresponding portion in an orientation from the fourth other-portion toward the fourth portion.

Configuration 18

The magnetic sensor according to Configuration 17, wherein
the first other-end portion is electrically connected with the second end portion,
the first end portion is electrically connected with the third end portion,
the third other-end portion is electrically connected with the fourth end portion,
the second other-end portion is electrically connected with the fourth other-end portion,
the element current circuit is configured to supply the element current between a first connection point and a second connection point,
the first connection point is between the first end portion and the third end portion, and
the second connection point is between the second other-end portion and the fourth other-end portion,
the first portion is electrically connected with the third portion,
the first other-portion is electrically connected with the second portion,
the third other-portion is electrically connected with the fourth portion,
the second other-portion is electrically connected with the fourth other-portion,
the first current circuit is configured to supply the first current between a fifth connection point and a sixth connection point,
the fifth connection point is between the first other-portion and the second portion, and
the sixth connection point is between the third other-portion and the fourth portion.

Configuration 19

The magnetic sensor according to Configuration 17 or 18, further comprising:
a detection circuit,
the detection circuit being configured to detect a change of a potential between a third connection point and a fourth connection point,
the third connection point being between the first other-end portion and the second end portion,
the fourth connection point being between the third other-end portion and the fourth end portion.

Configuration 20

An inspection device, comprising:
the magnetic sensor according to any one of Configurations 1 to 19; and
a processor configured to process a signal output from the magnetic sensor.

According to embodiments, a magnetic sensor and an inspection device can be provided in which the sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as magnetic elements, magnetic layers, nonmagnetic layers, magnetic members, conductive members, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, and inspection devices practicable by an appropriate design modification by one skilled in the art based on the magnetic sensors, and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising:
a first sensor part including
a first magnetic element,
a first side magnetic part, and
a first counter side magnetic part; and
a conductive member,
the conductive member including a first corresponding portion along the first magnetic element,
the first magnetic element including:
a first magnetic layer,
a first counter magnetic layer, a direction from the first magnetic layer toward the first counter magnetic layer being along a first direction, and
a first intermediate magnetic layer located between the first magnetic layer and the first counter magnetic layer,
the first side magnetic part including a first side magnetic layer,
the first counter side magnetic part including a first counter side magnetic layer,
the first intermediate magnetic layer being between the first side magnetic layer and the first counter side magnetic layer in a second direction crossing the first direction.

2. The magnetic sensor according to claim 1, wherein
a distance along the second direction between the first side magnetic part and the first magnetic element is not more than 0.01 times a first length along the second direction of the first magnetic element.

3. The sensor according to claim 1, wherein
the first magnetic element further includes:
a first nonmagnetic layer located between the first magnetic layer and the first intermediate magnetic layer; and
a first intermediate nonmagnetic layer located between the first intermediate magnetic layer and the first counter magnetic layer,
the first side magnetic part further includes a first stacked side magnetic layer,
the first counter side magnetic part further includes a first counter stacked side magnetic layer, and
the first counter magnetic layer is between the first stacked side magnetic layer and the first counter stacked side magnetic layer in the second direction.

4. The sensor according to claim 3, wherein
the first side magnetic part further includes a first side nonmagnetic layer located between the first side magnetic layer and the first stacked side magnetic layer,
the first counter side magnetic part further includes a first counter side nonmagnetic layer located between the first counter side magnetic layer and the first counter stacked side magnetic layer, and
the first side nonmagnetic layer and the first counter side nonmagnetic layer include a material included in the first intermediate nonmagnetic layer.

5. The sensor according to claim 1, wherein
a first length along the second direction of the first magnetic element is greater than a first width of the first magnetic element along a direction crossing a plane including the first and second directions.

6. The sensor according to claim 1, wherein
the first sensor part further includes a first magnetic member and a first counter magnetic member,
a direction from the first magnetic member toward the first counter magnetic member is along a third direction crossing a plane including the first and second directions, and
the first magnetic element overlaps a region between the first magnetic member and the first counter magnetic member in the first direction.

7. The sensor according to claim 6, wherein
a portion of the first magnetic element overlaps a portion of the first magnetic member in the first direction, and
an other portion of the first magnetic element overlaps a portion of the first counter magnetic member in the first direction.

8. The sensor according to claim 1, wherein
the first corresponding portion overlaps the first magnetic element in a direction crossing the second direction.

9. The sensor according to claim 8, wherein
the first magnetic element includes a first end portion and a first other-end portion,
a direction from the first end portion toward the first other-end portion is along the second direction,
the first corresponding portion includes a first portion and a first other-portion,
the first portion corresponds to the first end portion, and
the first other-portion corresponds to the first other-end portion.

10. The sensor according to claim 9, wherein
the first portion overlaps the first end portion in the first direction, and
the first other-portion overlaps the first other-end portion in the first direction.

11. The sensor according to claim 8, wherein
an electrical resistance of the first magnetic element has an even-function characteristic with respect to a current flowing in the first corresponding portion.

12. The sensor according to claim 1, wherein
an electrical resistance of the first magnetic element has an even-function characteristic with respect to a magnetic field applied to the first magnetic element.

13. The sensor according to claim 8, further comprising:
a second sensor part including a second magnetic element;
a third sensor part including a third magnetic element;
a fourth sensor part including a fourth magnetic element;
an element current circuit; and
a first current circuit,
the first magnetic element including a first end portion and a first other-end portion,
a direction from the first end portion toward the first other-end portion being along the second direction,
the second magnetic element including a second end portion and a second other-end portion,
a direction from the second end portion toward the second other-end portion being along the second direction,
the third magnetic element including a third end portion and a third other-end portion,
a direction from the third end portion toward the third other-end portion being along the second direction,
the fourth magnetic element including a fourth end portion and a fourth other-end portion,
a direction from the fourth end portion toward the fourth other-end portion being along the second direction,
the conductive member including
  a second corresponding portion along the second magnetic element,
  a third corresponding portion along the third magnetic element, and
  a fourth corresponding portion along the fourth magnetic element,
the first corresponding portion including a first portion and a first other-portion,
the first portion corresponding to the first end portion,
the first other-portion corresponding to the first other-end portion,
the second corresponding portion including a second portion and a second other-portion,
the second portion corresponding to the second end portion,
the second other-portion corresponding to the second other-end portion,
the third corresponding portion including a third portion and a third other-portion,
the third portion corresponding to the third end portion,
the third other-portion corresponding to the third other-end portion,
the fourth corresponding portion including a fourth portion and a fourth other-portion,
the fourth portion corresponding to the fourth end portion,
the fourth other-portion corresponding to the fourth other-end portion,
the element current circuit being configured to supply an element current to the first, second, third, and fourth magnetic elements,
the first current circuit being configured to supply a first current to the first, second, third, and fourth corresponding portions,
the first current including an alternating current component.

14. The sensor according to claim 13, wherein
at a first time at which the first current is supplied to the conductive member:
  the element current flows through the first magnetic element in an orientation from the first end portion toward the first other-end portion;
  the element current flows through the second magnetic element in an orientation from the second end portion toward the second other-end portion;
  the element current flows through the third magnetic element in an orientation from the third end portion toward the third other-end portion;
  the element current flows through the fourth magnetic element in an orientation from the fourth end portion toward the fourth other-end portion;
  the first current flows through the first corresponding portion in an orientation from the first other-portion toward the first portion;
  the first current flows through the second corresponding portion in an orientation from the second portion toward the second other-portion;
  the first current flows through the third corresponding portion in an orientation from the third portion toward the third other-portion; and
  the first current flows through the fourth corresponding portion in an orientation from the fourth other-portion toward the fourth portion.

15. The sensor according to claim 14, wherein
the first other-end portion is electrically connected with the second end portion,
the first end portion is electrically connected with the third end portion,
the third other-end portion is electrically connected with the fourth end portion,
the second other-end portion is electrically connected with the fourth other-end portion,
the element current circuit is configured to supply the element current between a first connection point and a second connection point,
the first connection point is between the first end portion and the third end portion, and
the second connection point is between the second other-end portion and the fourth other-end portion, the first portion is electrically connected with the third portion, the first other-portion is electrically connected with the second portion, the third other-portion is electrically connected with the fourth portion, the second other-portion is electrically connected with the fourth other-portion, the first current circuit is configured to supply the first current between a fifth connection point and a sixth connection point, the fifth connection point is between the first other-portion and the second portion, and the sixth connection point is between the third other-portion and the fourth portion.

16. The sensor according to claim 14, further comprising:

a detection circuit, the detection circuit being configured to detect a change of a potential between a third connection point and a fourth connection point, the third connection point being between the first other-end portion and the second end portion, the fourth connection point being between the third other-end portion and the fourth end portion.

17. An inspection device, comprising:

the magnetic sensor according to claim 1; and a processor configured to process a signal output from the magnetic sensor.

18. A magnetic sensor, comprising:

a first sensor part including
  a first magnetic element,
  a first stacked magnetic layer, and
  a first counter stacked magnetic layer; and a conductive member, the conductive member including a first corresponding portion along the first magnetic element, the first magnetic element including
  a first magnetic layer,
  a first counter magnetic layer, a direction from the first magnetic layer toward the first counter magnetic layer being along a first direction,
  a first intermediate magnetic layer located between the first magnetic layer and the first counter magnetic layer,
  a first nonmagnetic layer located between the first magnetic layer and the first intermediate magnetic layer, and
  a first intermediate nonmagnetic layer located between the first intermediate magnetic layer and the first counter magnetic layer, a direction from the first stacked magnetic layer toward the first counter stacked magnetic layer being along a second direction crossing the first direction, a portion of the first counter magnetic layer being between the first magnetic layer and the first stacked magnetic layer, an other portion of the first counter magnetic layer being between the first magnetic layer and the first counter stacked magnetic layer.

19. The sensor according to claim 18, wherein the first stacked magnetic layer contacts the portion of the first counter magnetic layer, or a distance along the first direction between the first stacked magnetic layer and the portion of the first counter magnetic layer is not more than 0.001 times a thickness of the first counter magnetic layer, and the first counter stacked magnetic layer contacts the other portion of the first counter magnetic layer, or a distance along the first direction between the first counter stacked magnetic layer and the other portion of the first counter magnetic layer is not more than 0.001 times the thickness of the first counter magnetic layer.

20. The sensor according to claim 18, wherein a length along the second direction of the first stacked magnetic layer is not less than 0.01 times and not more than 0.1 times a length along the second direction of the first magnetic element, and a length along the second direction of the first counter stacked magnetic layer is not less than 0.01 times and not more than 0.1 times the length along the second direction of the first magnetic element.

* * * * *